United States Patent [19]
Schmidt et al.

[11] Patent Number: 5,879,941
[45] Date of Patent: Mar. 9, 1999

[54] POLYPEPTIDES AND POLYNUCLEOTIDES RELATING TO THE α-AND β-SUBUNITS OF A GLUTAMATE DEHYDROGENASE AND METHODS OF USE

[75] Inventors: Robert R. Schmidt, Gainesville, Fla.; Philip Miller, Ballwin, Mo.

[73] Assignee: University of Florida, Gainesville, Fla.

[21] Appl. No.: 541,033

[22] Filed: Oct. 6, 1995

[51] Int. Cl.$^6$ .............................. C12N 5/10; C12N 15/00; C07H 21/04

[52] U.S. Cl. ....................... 435/419; 435/172.3; 435/424; 536/23.6

[58] Field of Search ........................ 536/23.6; 435/172.3, 435/419, 424

[56] References Cited

FOREIGN PATENT DOCUMENTS 9509911  4/1995  WIPO .

OTHER PUBLICATIONS

Napoli et al. Introduction of a chimeric chalcone synthase gene into petunia results in reversible co–suppresssion of homologous genes in trans. The Plant Cell. 2:279–289, 1990.

"Nicotinamide Adenine DI Nucleotide Glutamate Dejydrogenase Obtain Chlorella Cell Buffer Extract Two Stage Chromatography Phosphate Buffer Elution" (1982) Biochem. Inst., **abstract only.

Cock, J.M. et al. (1991) "A nuclear gene with many introns encoding ammonium–inducible chloroplastic NADP–specific glutamate dehydrogenase(s) in *Chlorella sorokiniana*" Plant Molecular Biology 17:1023–1044.

Bascomb, N.F. et al. (1987) "Different Rates of Synthesis and Degradation of Two Chloroplastic Ammonium–Inducible NADP–Specific Glutamate Dehydrogenase Isoenzymes during Induction and Deinduction in *Chlorella sorokiniana* Cells" Plant Physiol. 83:85–91.

Bascomb, N.F., R.R. Schmidt (1987) "Purification and Partial Kinetic and Physical Characterization of Two Chloroplast–Localized NADP–Specific Glutamate Dehydrogenase Isoenzymes and Their Preferential Accumulation of *Chlorella sorokiniana* Cells Cultures at Low or High Ammonium Levels" Plant Physiol. 83:75–84.

Prunkard, D.E. et al. (1986) "Effect of Different Carbon Sources on the Ammonium Induction of Different Forms of NADP–Specific Glutamate Dehydrogenase in *Chlorella sorokiniana* Cells Cultured in the Light and Dark" Plant Physiol. 81:413–422.

Yeung, A.T. et al. (1981) "Purification of an Ammonium–Inducible Glutamate Dehydrogenase and the Use of its Antigen Affinity Column–Purified Antibody in Specific Immunoprecipitation and Immunoadsorption Procedures" Analytical Biochemistry 110:216–228.

Meredith, M.J. et al. (1978) "Physical and Kinetic Properties of the Nicotinamide Adenine Dinucleotide–specific Glutamate Dehydrogenase Purified from *Chlorella sorokiniana*" Plant Physiol. 61:967–974.

Srivastava, H.S., R.P. Singh (1987) "Role and Regulation of L–Glutamate Dehydrogenase Activity in Higher Plants" Phytochemistry 26(3):597–610.

Prunkard, D.E. et al. (1986) "Evidence for Chloroplastic Localization of an Ammonium–Inducible Glutamate Dehydrogenase and Synthesis of its Subunit from a Cytosolic Precursor–Protein in *Chlorella sorokiniana*" Plant Physiol. 81:349–355.

Wallagrove, R.M. et al. (1987) "Barley Mutants Lacking Chloroplast Glutamine Synthetase–Biochemical and Genetic Analysis" Plant Physiol. 83:155–158.

Miller, P.W. et al. (1994) "Transcription initiation site of a NADP–specific glutamate dehydrogenase gene and potential use of its promoter region to express foreign genes in ammonium–cultured *Chlorella sorokiniana* cells" Journal of Applied Phycology 6:211–223.

Meredith, M.J., R.R. Schmidt (1991) "NAD–Specific glutamate dehydrogenase isoenzyme localised in mitochondria of nitrate–cultured *Chlorella sorokiniana* cells" Plant Physiol. 10:67–71.

Bascomb, N.F. et al. (1986) "Specific Polysome Innunoadsorption to Purify an Ammonium–Inducible Glutamate Dehydrogenase mRNA from *Chlorella sorokiniana* and Synthesis of Full Length Double–Stranded cDNA from the Purified mRNA" Plant Physiol. 81:527–532.

Miflin, B.J., P.J. Lea (1976) "The Pathway of Nitrogen Assimilation in Plants" Phytochemistry 15:873–885.

*Primary Examiner*—Douglas W. Robinson
*Assistant Examiner*—Thanda Wai
*Attorney, Agent, or Firm*—Saliwanchik, Lloyd & Saliwanchik

[57] ABSTRACT

Amino acid and nucleotide sequences relating to the glutamate dehydrogenase (GDH) enzyme are described. The GDH enzymes described herein were discovered in the alga *Chlorella sorokiniana* in the form of seven different inducible isoenzymes. These isoenzymes are found in the algae as chloroplast-localized hexamers composed of α- and β-subunits. Plants transformed with nucleotide sequences encoding the α- or β-subunits of the enzyme show improved properties, for example, increased growth and improved stress tolerance.

13 Claims, No Drawings

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
( A ) LENGTH: 2140 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 33..1610

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| CTCCTTTCTG | CTCGCCCTCT | CTCCGTCCCG | CC | ATG<br>Met<br>1 | CAG<br>Gln | ACC<br>Thr | GCC<br>Ala | CTC<br>Leu | GTC<br>Val<br>5 | GCC<br>Ala | | | | | | 53 |

| | | | | | | | | | | | | | | | |
|---|---|---|---|---|---|---|---|---|---|---|---|---|---|---|---|
| AAG<br>Lys | CCT<br>Pro | ATC<br>Ile<br>10 | GTG<br>Val | GCC<br>Ala | GCC<br>Ala | CCG<br>Pro | CTG<br>Leu<br>15 | GCG<br>Ala | GCA<br>Ala | CGC<br>Arg | CCG<br>Pro | CGC<br>Arg<br>20 | TGC<br>Cys | CTC<br>Leu | GCG<br>Ala | 101 |
| CCG<br>Pro | TGG<br>Trp<br>25 | CCG<br>Pro | TGC<br>Cys | GCG<br>Ala | TGG<br>Trp | GTC<br>Val<br>30 | CGC<br>Arg | TCC<br>Ser | GCC<br>Ala | AAG<br>Lys | CGC<br>Arg<br>35 | GAT<br>Asp | GTC<br>Val | CGC<br>Arg | GCC<br>Ala | 149 |
| AAG<br>Lys<br>40 | GCC<br>Ala | GTC<br>Val | TCG<br>Ser | CTG<br>Leu | GAG<br>Glu<br>45 | GAG<br>Glu | CAG<br>Gln | ATC<br>Ile | TCC<br>Ser | GCG<br>Ala<br>50 | ATG<br>Met | GAC<br>Asp | GCC<br>Ala | ACC<br>Thr | ACC<br>Thr<br>55 | 197 |
| GGC<br>Gly | GAC<br>Asp | TTC<br>Phe | ACG<br>Thr | GCG<br>Ala<br>60 | CTG<br>Leu | CAG<br>Gln | AAG<br>Lys | GCG<br>Ala | GTG<br>Val<br>65 | AAG<br>Lys | CAG<br>Gln | ATG<br>Met | GCC<br>Ala | ACC<br>Thr<br>70 | AAG<br>Lys | 245 |
| GCG<br>Ala | GGC<br>Gly | ACT<br>Thr | GAG<br>Glu<br>75 | GGC<br>Gly | CTG<br>Leu | GTG<br>Val | CAC<br>His | GGC<br>Gly<br>80 | ATC<br>Ile | AAG<br>Lys | AAC<br>Asn | CCC<br>Pro | GAC<br>Asp<br>85 | GTG<br>Val | CGC<br>Arg | 293 |
| CAG<br>Gln | CTG<br>Leu | CTG<br>Leu<br>90 | ACC<br>Thr | GAG<br>Glu | ATC<br>Ile | TTC<br>Phe | ATG<br>Met<br>95 | AAG<br>Lys | GAC<br>Asp | CCG<br>Pro | GAG<br>Glu | CAG<br>Gln<br>100 | CAG<br>Gln | GAG<br>Glu | TTC<br>Phe | 341 |
| ATG<br>Met | CAG<br>Gln<br>105 | GCG<br>Ala | GTG<br>Val | CGC<br>Arg | GAG<br>Glu | GTG<br>Val<br>110 | GCC<br>Ala | GTC<br>Val | TCC<br>Ser | CTG<br>Leu | CAG<br>Gln<br>115 | CCC<br>Pro | GTG<br>Val | TTC<br>Phe | GAG<br>Glu | 389 |
| AAG<br>Lys<br>120 | CGC<br>Arg | CCC<br>Pro | GAG<br>Glu | CTG<br>Leu | CTG<br>Leu<br>125 | CCC<br>Pro | ATC<br>Ile | TTC<br>Phe | AAG<br>Lys | CAG<br>Gln<br>130 | ATC<br>Ile | GTT<br>Val | GAG<br>Glu | CCT<br>Pro | GAG<br>Glu<br>135 | 437 |
| CGC<br>Arg | GTG<br>Val | ATC<br>Ile | ACC<br>Thr | TTC<br>Phe<br>140 | CGC<br>Arg | GTG<br>Val | TCC<br>Ser | TGG<br>Trp | CTG<br>Leu<br>145 | GAC<br>Asp | GAC<br>Asp | GCC<br>Ala | GGC<br>Gly | AAC<br>Asn<br>150 | CTG<br>Leu | 485 |
| CAG<br>Gln | GTC<br>Val | AAC<br>Asn | CGC<br>Arg<br>155 | GGC<br>Gly | TTC<br>Phe | CGC<br>Arg | GTG<br>Val | CAG<br>Gln<br>160 | TAC<br>Tyr | TCG<br>Ser | TCC<br>Ser | GCC<br>Ala | ATC<br>Ile<br>165 | GGC<br>Gly | CCC<br>Pro | 533 |
| TAC<br>Tyr | AAG<br>Lys | GGC<br>Gly<br>170 | GGC<br>Gly | CTG<br>Leu | CGC<br>Arg | TTC<br>Phe | CAC<br>His<br>175 | CCC<br>Pro | TCC<br>Ser | GTG<br>Val | AAC<br>Asn | CTG<br>Leu<br>180 | TCC<br>Ser | ATC<br>Ile | ATG<br>Met | 581 |
| AAG<br>Lys | TTC<br>Phe<br>185 | CTT<br>Leu | GCC<br>Ala | TTT<br>Phe | GAG<br>Glu | CAG<br>Gln<br>190 | ATC<br>Ile | TTC<br>Phe | AAG<br>Lys | AAC<br>Asn | AGC<br>Ser<br>195 | CTG<br>Leu | ACC<br>Thr | ACC<br>Thr | CTG<br>Leu | 629 |
| CCC<br>Pro<br>200 | ATG<br>Met | GGC<br>Gly | GGC<br>Gly | GGC<br>Gly | AAG<br>Lys<br>205 | GGC<br>Gly | GGC<br>Gly | TCC<br>Ser | GAC<br>Asp | TTC<br>Phe<br>210 | GAC<br>Asp | CCC<br>Pro | AAG<br>Lys | GGC<br>Gly | AAG<br>Lys<br>215 | 677 |
| AGC<br>Ser | GAC<br>Asp | GCG<br>Ala | GAG<br>Glu | GTG<br>Val<br>220 | ATG<br>Met | CGC<br>Arg | TTC<br>Phe | TGC<br>Cys | CAG<br>Gln<br>225 | TCC<br>Ser | TTC<br>Phe | ATG<br>Met | ACC<br>Thr | GAG<br>Glu<br>230 | CTG<br>Leu | 725 |
| CAG<br>Gln | CGC<br>Arg | CAC<br>His | ATC<br>Ile<br>235 | AGC<br>Ser | TAC<br>Tyr | GTG<br>Val | CAG<br>Gln | GAC<br>Asp<br>240 | GTG<br>Val | CCC<br>Pro | GCC<br>Ala | GGC<br>Gly | GAC<br>Asp<br>245 | ATC<br>Ile | GGC<br>Gly | 773 |
| GTG<br>Val | GGC<br>Gly | GCG<br>Ala<br>250 | CGC<br>Arg | GAG<br>Glu | ATT<br>Ile | GGC<br>Gly | TAC<br>Tyr<br>255 | CTT<br>Leu | TTC<br>Phe | GGC<br>Gly | CAG<br>Gln | TAC<br>Tyr<br>260 | AAG<br>Lys | CGC<br>Arg | ATC<br>Ile | 821 |
| ACC<br>Thr | AAG<br>Lys<br>265 | AAC<br>Asn | TAC<br>Tyr | ACC<br>Thr | GGC<br>Gly | GTG<br>Val<br>270 | CTG<br>Leu | ACC<br>Thr | CCG<br>Pro | AAG<br>Lys | GGC<br>Gly<br>275 | CAG<br>Gln | GAG<br>Glu | TAT<br>Tyr | GGC<br>Gly | 869 |
| GGC<br>Gly<br>280 | TCC<br>Ser | GAG<br>Glu | ATC<br>Ile | CGC<br>Arg | CCC<br>Pro<br>285 | GAG<br>Glu | GCC<br>Ala | ACC<br>Thr | GGC<br>Gly | TAC<br>Tyr<br>290 | GGC<br>Gly | GCC<br>Ala | GTG<br>Val | CTG<br>Leu | TTT<br>Phe<br>295 | 917 |

| | | | | | | | | | | | | | | | | |
|---|---|---|---|---|---|---|---|---|---|---|---|---|---|---|---|---|
| GTG | GAG | AAC | GTG | CTG | AAG | GAC | AAG | GGC | GAG | AGC | CTC | AAG | GGC | AAG | CGC | 965 |
| Val | Glu | Asn | Val | Leu 300 | Lys | Asp | Lys | Gly | Glu 305 | Ser | Leu | Lys | Gly | Lys 310 | Arg | |
| TGC | CTG | GTG | TCT | GGC | GCG | GGC | AAC | GTG | GCC | CAG | TAC | TGC | GCG | GAG | CTG | 1013 |
| Cys | Leu | Val | Ser 315 | Gly | Ala | Gly | Asn | Val 320 | Ala | Gln | Tyr | Cys | Ala 325 | Glu | Leu | |
| CTG | CTG | GAG | AAG | GGC | GCC | ATC | GTG | CTG | TCG | CTG | TCC | GAC | TCC | CAG | GGC | 1061 |
| Leu | Leu | Glu 330 | Lys | Gly | Ala | Ile | Val 335 | Leu | Ser | Leu | Ser | Asp 340 | Ser | Gln | Gly | |
| TAC | GTG | TAC | GAG | CCC | AAC | GGC | TTC | ACG | CGC | GAG | CAG | CTG | CAG | GCG | GTG | 1109 |
| Tyr | Val | Tyr 345 | Glu | Pro | Asn | Gly | Phe 350 | Thr | Arg | Glu | Gln | Leu 355 | Gln | Ala | Val | |
| CAG | GAC | ATG | AAG | AAG | AAG | AAC | AAC | AGC | GCC | CGC | ATC | TCC | GAG | TAC | AAG | 1157 |
| Gln 360 | Asp | Met | Lys | Lys | Lys 365 | Asn | Asn | Ser | Ala | Arg 370 | Ile | Ser | Glu | Tyr | Lys 375 | |
| AGC | GAC | ACC | GCC | GTG | TAT | GTG | GGC | GAC | CGC | CGC | AAG | CCT | TGG | GAG | CTG | 1205 |
| Ser | Asp | Thr | Ala | Val 380 | Tyr | Val | Gly | Asp | Arg 385 | Arg | Lys | Pro | Trp | Glu 390 | Leu | |
| GAC | TGC | CAG | GTG | GAC | ATC | GCC | TTC | CCC | TGC | GCC | ACC | CAG | AAC | GAG | ATC | 1253 |
| Asp | Cys | Gln | Val 395 | Asp | Ile | Ala | Phe | Pro 400 | Cys | Ala | Thr | Gln | Asn 405 | Glu | Ile | |
| GAT | GAG | CAC | GAC | GCC | GAG | CTG | CTG | ATC | AAG | CAC | GGC | TGC | CAG | TAC | GTG | 1301 |
| Asp | Glu | His 410 | Asp | Ala | Glu | Leu | Leu 415 | Ile | Lys | His | Gly | Cys 420 | Gln | Tyr | Val | |
| GTG | GAG | GGC | GCC | AAC | ATG | CCC | TCC | ACC | AAC | GAG | GCC | ATC | CAC | AAG | TAC | 1349 |
| Val | Glu | Gly | Ala | Asn 425 | Met | Pro | Ser | Thr | Asn 430 | Glu | Ala | Ile | His | Lys 435 | Tyr | |
| AAC | AAG | GCC | GGC | ATC | ATC | TAC | TGC | CCC | GGC | AAG | GCG | GCC | AAC | GCC | GGC | 1397 |
| Asn 440 | Lys | Ala | Gly | Ile | Ile 445 | Tyr | Cys | Pro | Gly | Lys 450 | Ala | Ala | Asn | Ala | Gly 455 | |
| GGC | GTG | GCG | GTC | AGC | GGC | CTG | GAG | ATG | ACC | CAG | AAC | CGC | ATG | AGC | CTG | 1445 |
| Gly | Val | Ala | Val | Ser 460 | Gly | Leu | Glu | Met | Thr 465 | Gln | Asn | Arg | Met | Ser 470 | Leu | |
| AAC | TGG | ACT | CGC | GAG | GAG | GTT | CGC | GAC | AAG | CTG | GAG | CGC | ATC | ATG | AAG | 1493 |
| Asn | Trp | Thr | Arg 475 | Glu | Glu | Val | Arg | Asp 480 | Lys | Leu | Glu | Arg | Ile 485 | Met | Lys | |
| GAC | ATC | TAC | GAC | TCC | GCC | ATG | GGG | CCG | TCC | CGC | AGA | TAC | AAT | GTT | GAC | 1541 |
| Asp | Ile | Tyr 490 | Asp | Ser | Ala | Met | Gly 495 | Pro | Ser | Arg | Arg | Tyr 500 | Asn | Val | Asp | |
| CTG | GCT | GCG | GGC | GCC | AAC | ATC | GCG | GGC | TTC | ACC | AAG | GTG | GCT | GAT | GCC | 1589 |
| Leu | Ala | Ala 505 | Gly | Ala | Asn | Ile | Ala 510 | Gly | Phe | Thr | Lys | Val 515 | Ala | Asp | Ala | |
| GTC | AAG | GCC | CAG | GGC | GCT | GTT | TAAGCTGCCC | AGGCCCAAGC | CACGGCTCAC | | | | | | | 1640 |
| Val 520 | Lys | Ala | Gln | Gly | Ala 525 | Val | | | | | | | | | | |

| | | | | |
|---|---|---|---|---|
| CGGCAATCCA | ACCCAACCAA | CTCAACGGCC | AGGACCTTTT | CGGAAGCGGC GCCTTTTTCC | 1700 |
| CAGCCAGGGC | CCTCACCTGC | CCTTTCATAA | CCCTGCTATT | GCCGCCGTGC CCCTGCAATT | 1760 |
| CCACCCCAAG | AAGAACTAGC | GGCACTTGAC | TGCATCAGGA | CGGCTATTTT TTTCGCGACG | 1820 |
| CGCGCTCACC | CCGAGAGCCT | CTCTCCCCCG | AGCCCTAAGC | GCTGACGTCC GCCCGACTTT | 1880 |
| GCCTCGCACA | TCGCTCGGTT | TTGACCCCCT | CCAGTCTACC | CACCCTGTTG TGAAGCCTAC | 1940 |
| CAGCTCAATT | GCCTTTTAGT | GTATGTGCGC | CCCCTCCTGC | CCCCGAATTT TCCTGCCATG | 2000 |
| AGACGTGCGG | TTCCTAGCCT | GGTGACCCCA | AGTAGCAGTT | AGTGTGCGTG CCTTGCCCTG | 2060 |
| CGCTGCCCGG | GATGCGATAC | TGTGACCTGA | GAGTGCTTGT | GTAAACACGA CGAGTCAAAA | 2120 |
| AAAAAAAAAA | AAAAAAAAAA | | | | 2140 |

( 2 ) INFORMATION FOR SEQ ID NO:2:

(i) SEQUENCE CHARACTERISTICS:
   (A) LENGTH: 526 amino acids
   (B) TYPE: amino acid
   (D) TOPOLOGY: linear (ii) MOLECULE TYPE: protein (xi) SEQUENCE DESCRIPTION: SEQ ID NO:2:

```
Met Gln Thr Ala Leu Val Ala Lys Pro Ile Val Ala Ala Pro Leu Ala
 1               5                  10                  15

Ala Arg Pro Arg Cys Leu Ala Pro Trp Pro Cys Ala Trp Val Arg Ser
             20                  25                  30

Ala Lys Arg Asp Val Arg Ala Lys Ala Val Ser Leu Glu Glu Gln Ile
             35                  40                  45

Ser Ala Met Asp Ala Thr Thr Gly Asp Phe Thr Ala Leu Gln Lys Ala
         50                  55                  60

Val Lys Gln Met Ala Thr Lys Ala Gly Thr Glu Gly Leu Val His Gly
 65                  70                  75                  80

Ile Lys Asn Pro Asp Val Arg Gln Leu Leu Thr Glu Ile Phe Met Lys
                 85                  90                  95

Asp Pro Glu Gln Gln Glu Phe Met Gln Ala Val Arg Glu Val Ala Val
                100                 105                 110

Ser Leu Gln Pro Val Phe Glu Lys Arg Pro Glu Leu Leu Pro Ile Phe
            115                 120                 125

Lys Gln Ile Val Glu Pro Glu Arg Val Ile Thr Phe Arg Val Ser Trp
    130                 135                 140

Leu Asp Asp Ala Gly Asn Leu Gln Val Asn Arg Gly Phe Arg Val Gln
145                 150                 155                 160

Tyr Ser Ser Ala Ile Gly Pro Tyr Lys Gly Gly Leu Arg Phe His Pro
                165                 170                 175

Ser Val Asn Leu Ser Ile Met Lys Phe Leu Ala Phe Glu Gln Ile Phe
            180                 185                 190

Lys Asn Ser Leu Thr Thr Leu Pro Met Gly Gly Gly Lys Gly Gly Ser
    195                 200                 205

Asp Phe Asp Pro Lys Gly Lys Ser Asp Ala Glu Val Met Arg Phe Cys
210                 215                 220

Gln Ser Phe Met Thr Glu Leu Gln Arg His Ile Ser Tyr Val Gln Asp
225                 230                 235                 240

Val Pro Ala Gly Asp Ile Gly Val Gly Ala Arg Glu Ile Gly Tyr Leu
                245                 250                 255

Phe Gly Gln Tyr Lys Arg Ile Thr Lys Asn Tyr Thr Gly Val Leu Thr
            260                 265                 270

Pro Lys Gly Gln Glu Tyr Gly Gly Ser Glu Ile Arg Pro Glu Ala Thr
    275                 280                 285

Gly Tyr Gly Ala Val Leu Phe Val Glu Asn Val Leu Lys Asp Lys Gly
290                 295                 300

Glu Ser Leu Lys Gly Lys Arg Cys Leu Val Ser Gly Ala Gly Asn Val
305                 310                 315                 320

Ala Gln Tyr Cys Ala Glu Leu Leu Leu Glu Lys Gly Ala Ile Val Leu
                325                 330                 335

Ser Leu Ser Asp Ser Gln Gly Tyr Val Tyr Glu Pro Asn Gly Phe Thr
            340                 345                 350

Arg Glu Gln Leu Gln Ala Val Gln Asp Met Lys Lys Lys Asn Asn Ser
    355                 360                 365
```

```
Ala  Arg  Ile  Ser  Glu  Tyr  Lys  Ser  Asp  Thr  Ala  Val  Tyr  Val  Gly  Asp
     370                 375                 380

Arg  Arg  Lys  Pro  Trp  Glu  Leu  Asp  Cys  Gln  Val  Asp  Ile  Ala  Phe  Pro
385                      390                 395                           400

Cys  Ala  Thr  Gln  Asn  Glu  Ile  Asp  Glu  His  Asp  Ala  Glu  Leu  Leu  Ile
                    405                      410                      415

Lys  His  Gly  Cys  Gln  Tyr  Val  Val  Glu  Gly  Ala  Asn  Met  Pro  Ser  Thr
                    420                 425                      430

Asn  Glu  Ala  Ile  His  Lys  Tyr  Asn  Lys  Ala  Gly  Ile  Ile  Tyr  Cys  Pro
          435                      440                      445

Gly  Lys  Ala  Ala  Asn  Ala  Gly  Gly  Val  Ala  Val  Ser  Gly  Leu  Glu  Met
     450                      455                      460

Thr  Gln  Asn  Arg  Met  Ser  Leu  Asn  Trp  Thr  Arg  Glu  Glu  Val  Arg  Asp
465                      470                      475                      480

Lys  Leu  Glu  Arg  Ile  Met  Lys  Asp  Ile  Tyr  Asp  Ser  Ala  Met  Gly  Pro
                    485                      490                      495

Ser  Arg  Arg  Tyr  Asn  Val  Asp  Leu  Ala  Ala  Gly  Ala  Asn  Ile  Ala  Gly
                    500                      505                      510

Phe  Thr  Lys  Val  Ala  Asp  Ala  Val  Lys  Ala  Gln  Gly  Ala  Val
                    515                 520                 525
```

( 2 ) INFORMATION FOR SEQ ID NO:3:

( i ) SEQUENCE CHARACTERISTICS:
        ( A ) LENGTH: 2099 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 33..1568

( x i ) SEQUENCE DESCRIPTION: SEQ ID NO:3:

```
CTCCTTTCTG  CTCGCCTCT  CTCCGTCCCG  CC  ATG  CAG  ACC  GCC  CTC  GTC  GCC       53
                                      Met  Gln  Thr  Ala  Leu  Val  Ala
                                       1                    5

AAG  CCT  ATC  GTG  GCC  TGC  GCG  TGG  GTC  CGC  TCC  GCC  AAG  CGC  GAT  GTC  101
Lys  Pro  Ile  Val  Ala  Cys  Ala  Trp  Val  Arg  Ser  Ala  Lys  Arg  Asp  Val
               10                      15                 20

CGC  GCC  AAG  GCC  GTC  TCG  CTG  GAG  GAG  CAG  ATC  TCC  GCG  ATG  GAC  GCC  149
Arg  Ala  Lys  Ala  Val  Ser  Leu  Glu  Glu  Gln  Ile  Ser  Ala  Met  Asp  Ala
          25                      30                      35

ACC  ACC  GGC  GAC  TTC  ACG  GCG  CTG  CAG  AAG  GCG  GTG  AAG  CAG  ATG  GCC  197
Thr  Thr  Gly  Asp  Phe  Thr  Ala  Leu  Gln  Lys  Ala  Val  Lys  Gln  Met  Ala
40                       45                      50                      55

ACC  AAG  GCG  GGC  ACT  GAG  GGC  CTG  GTG  CAC  GGC  ATC  AAG  AAC  CCC  GAC  245
Thr  Lys  Ala  Gly  Thr  Glu  Gly  Leu  Val  His  Gly  Ile  Lys  Asn  Pro  Asp
                    60                      65                      70

GTG  CGC  CAG  CTG  CTG  ACC  GAG  ATC  TTC  ATG  AAG  GAC  CCG  GAG  CAG  CAG  293
Val  Arg  Gln  Leu  Leu  Thr  Glu  Ile  Phe  Met  Lys  Asp  Pro  Glu  Gln  Gln
               75                      80                      85

GAG  TTC  ATG  CAG  GCG  GTG  CGC  GAG  GTG  GCC  GTC  TCC  CTG  CAG  CCC  GTG  341
Glu  Phe  Met  Gln  Ala  Val  Arg  Glu  Val  Ala  Val  Ser  Leu  Gln  Pro  Val
          90                      95                      100

TTC  GAG  AAG  CGC  CCC  GAG  CTG  CTG  CCC  ATC  TTC  AAG  CAG  ATC  GTT  GAG  389
Phe  Glu  Lys  Arg  Pro  Glu  Leu  Leu  Pro  Ile  Phe  Lys  Gln  Ile  Val  Glu
     105                     110                     115
```

| | | | | | | | | | | | | | | | | |
|---|---|---|---|---|---|---|---|---|---|---|---|---|---|---|---|---|
| CCT | GAG | CGC | GTG | ATC | ACC | TTC | CGC | GTG | TCC | TGG | CTG | GAC | GAC | GCC | GGC | 437 |
| Pro 120 | Glu | Arg | Val | Ile | Thr 125 | Phe | Arg | Val | Ser | Trp 130 | Leu | Asp | Asp | Ala | Gly 135 | |
| AAC | CTG | CAG | GTC | AAC | CGC | GGC | TTC | CGC | GTG | CAG | TAC | TCG | TCC | GCC | ATC | 485 |
| Asn | Leu | Gln | Val | Asn 140 | Arg | Gly | Phe | Arg | Val 145 | Gln | Tyr | Ser | Ser | Ala 150 | Ile | |
| GGC | CCC | TAC | AAG | GGC | GGC | CTG | CGC | TTC | CAC | CCC | TCC | GTG | AAC | CTG | TCC | 533 |
| Gly | Pro | Tyr | Lys 155 | Gly | Gly | Leu | Arg | Phe 160 | His | Pro | Ser | Val | Asn 165 | Leu | Ser | |
| ATC | ATG | AAG | TTC | CTT | GCC | TTT | GAG | CAG | ATC | TTC | AAG | AAC | AGC | CTG | ACC | 581 |
| Ile | Met | Lys 170 | Phe | Leu | Ala | Phe | Glu 175 | Gln | Ile | Phe | Lys | Asn 180 | Ser | Leu | Thr | |
| ACC | CTG | CCC | ATG | GGC | GGC | GGC | AAG | GGC | GGC | TCC | GAC | TTC | GAC | CCC | AAG | 629 |
| Thr | Leu 185 | Pro | Met | Gly | Gly | Gly 190 | Lys | Gly | Gly | Ser | Asp 195 | Phe | Asp | Pro | Lys | |
| GGC | AAG | AGC | GAC | GCG | GAG | GTG | ATG | CGC | TTC | TGC | CAG | TCC | TTC | ATG | ACC | 677 |
| Gly 200 | Lys | Ser | Asp | Ala | Glu 205 | Val | Met | Arg | Phe | Cys 210 | Gln | Ser | Phe | Met | Thr 215 | |
| GAG | CTG | CAG | CGC | CAC | ATC | AGC | TAC | GTG | CAG | GAC | GTG | CCC | GCC | GGC | GAC | 725 |
| Glu | Leu | Gln | Arg | His 220 | Ile | Ser | Tyr | Val | Gln 225 | Asp | Val | Pro | Ala | Gly 230 | Asp | |
| ATC | GGC | GTG | GGC | GCG | CGC | GAG | ATT | GGC | TAC | CTT | TTC | GGC | CAG | TAC | AAG | 773 |
| Ile | Gly | Val | Gly 235 | Ala | Arg | Glu | Ile | Gly 240 | Tyr | Leu | Phe | Gly | Gln 245 | Tyr | Lys | |
| CGC | ATC | ACC | AAG | AAC | TAC | ACC | GGC | GTG | CTG | ACC | CCG | AAG | GGC | CAG | GAG | 821 |
| Arg | Ile | Thr 250 | Lys | Asn | Tyr | Thr | Gly 255 | Val | Leu | Thr | Pro | Lys 260 | Gly | Gln | Glu | |
| TAT | GGC | GGC | TCC | GAG | ATC | CGC | CCC | GAG | GCC | ACC | GGC | TAC | GGC | GCC | GTG | 869 |
| Tyr | Gly 265 | Gly | Ser | Glu | Ile | Arg 270 | Pro | Glu | Ala | Thr | Gly 275 | Tyr | Gly | Ala | Val | |
| CTG | TTT | GTG | GAG | AAC | GTG | CTG | AAG | GAC | AAG | GGC | GAG | AGC | CTC | AAG | GGC | 917 |
| Leu 280 | Phe | Val | Glu | Asn | Val 285 | Leu | Lys | Asp | Lys | Gly 290 | Glu | Ser | Leu | Lys | Gly 295 | |
| AAG | CGC | TGC | CTG | GTG | TCT | GGC | GCG | GGC | AAC | GTG | GCC | CAG | TAC | TGC | GCG | 965 |
| Lys | Arg | Cys | Leu | Val 300 | Ser | Gly | Ala | Gly | Asn 305 | Val | Ala | Gln | Tyr | Cys 310 | Ala | |
| GAG | CTG | CTG | CTG | GAG | AAG | GGC | GCC | ATC | GTG | CTG | TCG | CTG | TCC | GAC | TCC | 1013 |
| Glu | Leu | Leu | Leu 315 | Glu | Lys | Gly | Ala | Ile 320 | Val | Leu | Ser | Leu | Ser 325 | Asp | Ser | |
| CAG | GGC | TAC | GTG | TAC | GAG | CCC | AAC | GGC | TTC | ACG | CGC | GAG | CAG | CTG | CAG | 1061 |
| Gln | Gly | Tyr 330 | Val | Tyr | Glu | Pro | Asn 335 | Gly | Phe | Thr | Arg | Glu 340 | Gln | Leu | Gln | |
| GCG | GTG | CAG | GAC | ATG | AAG | AAG | AAG | AAC | AAC | AGC | GCC | CGC | ATC | TCC | GAG | 1109 |
| Ala | Val 345 | Gln | Asp | Met | Lys 350 | Lys | Lys | Asn | Asn | Ser 355 | Ala | Arg | Ile | Ser | Glu | |
| TAC | AAG | AGC | GAC | ACC | GCC | GTG | TAT | GTG | GGC | GAC | CGC | CGC | AAG | CCT | TGG | 1157 |
| Tyr | Lys | Ser | Asp 360 | Thr | Ala | Val | Tyr | Val 365 | Gly | Asp | Arg | Arg 370 | Lys | Pro | Trp 375 | |
| GAG | CTG | GAC | TGC | CAG | GTG | GAC | ATC | GCC | TTC | CCC | TGC | GCC | ACC | CAG | AAC | 1205 |
| Glu | Leu | Asp | Cys | Gln 380 | Val | Asp | Ile | Ala | Phe 385 | Pro | Cys | Ala | Thr | Gln 390 | Asn | |
| GAG | ATC | GAT | GAG | CAC | GAC | GCC | GAG | CTG | CTG | ATC | AAG | CAC | GGC | TGC | CAG | 1253 |
| Glu | Ile | Asp | Glu | His 395 | Asp | Ala | Glu | Leu | Leu 400 | Ile | Lys | His | Gly | Cys 405 | Gln | |
| TAC | GTG | GTG | GAG | GGC | GCC | AAC | ATG | CCC | TCC | ACC | AAC | GAG | GCC | ATC | CAC | 1301 |
| Tyr | Val | Val | Glu 410 | Gly | Ala | Asn | Met | Pro 415 | Ser | Thr | Asn | Glu | Ala 420 | Ile | His | |
| AAG | TAC | AAC | AAG | GCC | GGC | ATC | ATC | TAC | TGC | CCC | GGC | AAG | GCG | GCC | AAC | 1349 |
| Lys | Tyr | Asn | Lys 425 | Ala | Gly | Ile | Ile | Tyr 430 | Cys | Pro | Gly | Lys | Ala 435 | Ala | Asn | |

| | | | | | | | | | | | | | | | | |
|---|---|---|---|---|---|---|---|---|---|---|---|---|---|---|---|---|
| GCC | GGC | GGC | GTG | GCG | GTC | AGC | GGC | CTG | GAG | ATG | ACC | CAG | AAC | CGC | ATG | 1397 |
| Ala | Gly | Gly | Val | Ala | Val | Ser | Gly | Leu | Glu | Met | Thr | Gln | Asn | Arg | Met | |
| 440 | | | | 445 | | | | | 450 | | | | | 455 | | |
| AGC | CTG | AAC | TGG | ACT | CGC | GAG | GAG | GTT | CGC | GAC | AAG | CTG | GAG | CGC | ATC | 1445 |
| Ser | Leu | Asn | Trp | Thr | Arg | Glu | Glu | Val | Arg | Asp | Lys | Leu | Glu | Arg | Ile | |
| | | | | 460 | | | | 465 | | | | | 470 | | | |
| ATG | AAG | GAC | ATC | TAC | GAC | TCC | GCC | ATG | GGG | CCG | TCC | CGC | AGA | TAC | AAT | 1493 |
| Met | Lys | Asp | Ile | Tyr | Asp | Ser | Ala | Met | Gly | Pro | Ser | Arg | Arg | Tyr | Asn | |
| | | | 475 | | | | | 480 | | | | | 485 | | | |
| GTT | GAC | CTG | GCT | GCG | GGC | GCC | AAC | ATC | GCG | GGC | TTC | ACC | AAG | GTG | GCT | 1541 |
| Val | Asp | Leu | Ala | Ala | Gly | Ala | Asn | Ile | Ala | Gly | Phe | Thr | Lys | Val | Ala | |
| | | 490 | | | | | 495 | | | | | 500 | | | | |
| GAT | GCC | GTC | AAG | GCC | CAG | GGC | GCT | GTT | TAAGCTGCCC | AGGCCCAAGC | | | | | | 1588 |
| Asp | Ala | Val | Lys | Ala | Gln | Gly | Ala | Val | | | | | | | | |
| | 505 | | | | 510 | | | | | | | | | | | |

| | | | | | |
|---|---|---|---|---|---|
| CACGGCTCAC | CGGCAATCCA | ACCCAACCAA | CTCAACGGCC | AGGACCTTTT | CGGAAGCGGC | 1648 |
| GCCTTTTTCC | CAGCCAGGGC | CCTCACCTGC | CCTTTCATAA | CCCTGCTATT | GCCGCCGTGC | 1708 |
| CCCTGCAATT | CCACCCCAAG | AAGAACTAGC | GGCACTTGAC | TGCATCAGGA | CGGCTATTTT | 1768 |
| TTTCGCGACG | CGCGCTCACC | CCGAGAGCCT | CTCTCCCCG | AGCCCTAAGC | GCTGACGTCC | 1828 |
| GCCCGACTTT | GCCTCGCACA | TCGCTCGGTT | TTGACCCCCT | CCAGTCTACC | CACCCTGTTG | 1888 |
| TGAAGCCTAC | CAGCTCAATT | GCCTTTTAGT | GTATGTGCGC | CCCCTCCTGC | CCCCGAATTT | 1948 |
| TCCTGCCATG | AGACGTGCGG | TTCCTAGCCT | GGTGACCCCA | AGTAGCAGTT | AGTGTGCGTG | 2008 |
| CCTTGCCCTG | CGCTGCCCGG | GATGCGATAC | TGTGACCTGA | GAGTGCTTGT | GTAAACACGA | 2068 |
| CGAGTCAAAA | AAAAAAAAA | AAAAAAAAA | A | | | 2099 |

(2) INFORMATION FOR SEQ ID NO:4:

(i) SEQUENCE CHARACTERISTICS:
        (A) LENGTH: 512 amino acids
        (B) TYPE: amino acid
        (D) TOPOLOGY: linear (ii) MOLECULE TYPE: protein (xi) SEQUENCE DESCRIPTION: SEQ ID NO:4:

| | | | | | | | | | | | | | | |
|---|---|---|---|---|---|---|---|---|---|---|---|---|---|---|
| Met | Gln | Thr | Ala | Leu | Val | Ala | Lys | Pro | Ile | Val | Ala | Cys | Ala | Trp | Val |
| 1 | | | | 5 | | | | | 10 | | | | | 15 | |
| Arg | Ser | Ala | Lys | Arg | Asp | Val | Arg | Ala | Lys | Ala | Val | Ser | Leu | Glu | Glu |
| | | | 20 | | | | | 25 | | | | | 30 | | |
| Gln | Ile | Ser | Ala | Met | Asp | Ala | Thr | Thr | Gly | Asp | Phe | Thr | Ala | Leu | Gln |
| | | 35 | | | | | 40 | | | | | 45 | | | |
| Lys | Ala | Val | Lys | Gln | Met | Ala | Thr | Lys | Ala | Gly | Thr | Glu | Gly | Leu | Val |
| | 50 | | | | | 55 | | | | | 60 | | | | |
| His | Gly | Ile | Lys | Asn | Pro | Asp | Val | Arg | Gln | Leu | Leu | Thr | Glu | Ile | Phe |
| 65 | | | | | 70 | | | | | 75 | | | | | 80 |
| Met | Lys | Asp | Pro | Glu | Gln | Gln | Glu | Phe | Met | Gln | Ala | Val | Arg | Glu | Val |
| | | | | 85 | | | | | 90 | | | | | 95 | |
| Ala | Val | Ser | Leu | Gln | Pro | Val | Phe | Glu | Lys | Arg | Pro | Glu | Leu | Leu | Pro |
| | | | 100 | | | | | 105 | | | | | 110 | | |
| Ile | Phe | Lys | Gln | Ile | Val | Glu | Pro | Glu | Arg | Val | Ile | Thr | Phe | Arg | Val |
| | | 115 | | | | | 120 | | | | | 125 | | | |
| Ser | Trp | Leu | Asp | Asp | Ala | Gly | Asn | Leu | Gln | Val | Asn | Arg | Gly | Phe | Arg |
| | 130 | | | | | 135 | | | | | 140 | | | | |
| Val | Gln | Tyr | Ser | Ser | Ala | Ile | Gly | Pro | Tyr | Lys | Gly | Gly | Leu | Arg | Phe |
| 145 | | | | | 150 | | | | | 155 | | | | | 160 |

| His | Pro | Ser | Val | Asn | Leu | Ser | Ile | Met | Lys | Phe | Leu | Ala | Phe | Glu | Gln |
|---|---|---|---|---|---|---|---|---|---|---|---|---|---|---|---|
| | | | | 165 | | | | 170 | | | | | | 175 | |
| Ile | Phe | Lys | Asn | Ser | Leu | Thr | Thr | Leu | Pro | Met | Gly | Gly | Gly | Lys | Gly |
| | | | 180 | | | | | 185 | | | | | 190 | | |
| Gly | Ser | Asp | Phe | Asp | Pro | Lys | Gly | Lys | Ser | Asp | Ala | Glu | Val | Met | Arg |
| | | 195 | | | | | 200 | | | | | 205 | | | |
| Phe | Cys | Gln | Ser | Phe | Met | Thr | Glu | Leu | Gln | Arg | His | Ile | Ser | Tyr | Val |
| | 210 | | | | | 215 | | | | | 220 | | | | |
| Gln | Asp | Val | Pro | Ala | Gly | Asp | Ile | Gly | Val | Gly | Ala | Arg | Glu | Ile | Gly |
| 225 | | | | | 230 | | | | | 235 | | | | | 240 |
| Tyr | Leu | Phe | Gly | Gln | Tyr | Lys | Arg | Ile | Thr | Lys | Asn | Tyr | Thr | Gly | Val |
| | | | | 245 | | | | | 250 | | | | | 255 | |
| Leu | Thr | Pro | Lys | Gly | Gln | Glu | Tyr | Gly | Gly | Ser | Glu | Ile | Arg | Pro | Glu |
| | | | 260 | | | | | 265 | | | | | 270 | | |
| Ala | Thr | Gly | Tyr | Gly | Ala | Val | Leu | Phe | Val | Glu | Asn | Val | Leu | Lys | Asp |
| | | 275 | | | | | 280 | | | | | 285 | | | |
| Lys | Gly | Glu | Ser | Leu | Lys | Gly | Lys | Arg | Cys | Leu | Val | Ser | Gly | Ala | Gly |
| | 290 | | | | | 295 | | | | | 300 | | | | |
| Asn | Val | Ala | Gln | Tyr | Cys | Ala | Glu | Leu | Leu | Leu | Glu | Lys | Gly | Ala | Ile |
| 305 | | | | | 310 | | | | | 315 | | | | | 320 |
| Val | Leu | Ser | Leu | Ser | Asp | Ser | Gln | Gly | Tyr | Val | Tyr | Glu | Pro | Asn | Gly |
| | | | | 325 | | | | | 330 | | | | | 335 | |
| Phe | Thr | Arg | Glu | Gln | Leu | Gln | Ala | Val | Gln | Asp | Met | Lys | Lys | Lys | Asn |
| | | | 340 | | | | | 345 | | | | | 350 | | |
| Asn | Ser | Ala | Arg | Ile | Ser | Glu | Tyr | Lys | Ser | Asp | Thr | Ala | Val | Tyr | Val |
| | | 355 | | | | | 360 | | | | | 365 | | | |
| Gly | Asp | Arg | Arg | Lys | Pro | Trp | Glu | Leu | Asp | Cys | Gln | Val | Asp | Ile | Ala |
| | 370 | | | | | 375 | | | | | 380 | | | | |
| Phe | Pro | Cys | Ala | Thr | Gln | Asn | Glu | Ile | Asp | Glu | His | Asp | Ala | Glu | Leu |
| 385 | | | | | 390 | | | | | 395 | | | | | 400 |
| Leu | Ile | Lys | His | Gly | Cys | Gln | Tyr | Val | Val | Glu | Gly | Ala | Asn | Met | Pro |
| | | | | 405 | | | | | 410 | | | | | 415 | |
| Ser | Thr | Asn | Glu | Ala | Ile | His | Lys | Tyr | Asn | Lys | Ala | Gly | Ile | Ile | Tyr |
| | | | 420 | | | | | 425 | | | | | 430 | | |
| Cys | Pro | Gly | Lys | Ala | Ala | Asn | Ala | Gly | Gly | Val | Ala | Val | Ser | Gly | Leu |
| | | 435 | | | | | 440 | | | | | 445 | | | |
| Glu | Met | Thr | Gln | Asn | Arg | Met | Ser | Leu | Asn | Trp | Thr | Arg | Glu | Glu | Val |
| | 450 | | | | | 455 | | | | | 460 | | | | |
| Arg | Asp | Lys | Leu | Glu | Arg | Ile | Met | Lys | Asp | Ile | Tyr | Asp | Ser | Ala | Met |
| 465 | | | | | 470 | | | | | 475 | | | | | 480 |
| Gly | Pro | Ser | Arg | Arg | Tyr | Asn | Val | Asp | Leu | Ala | Ala | Gly | Ala | Asn | Ile |
| | | | | 485 | | | | | 490 | | | | | 495 | |
| Ala | Gly | Phe | Thr | Lys | Val | Ala | Asp | Ala | Val | Lys | Ala | Gln | Gly | Ala | Val |
| | | | 500 | | | | | 505 | | | | | 510 | | |

( 2 ) INFORMATION FOR SEQ ID NO:5:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
       Ala Val Ser Leu Glu Glu Gln Ile Ser Ala Met Asp Ala Thr Thr Gly
       1               5                   10                  15

Asp Phe Thr Ala
                   20
```

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
       Asp Ala Thr Thr Gly Asp Phe Thr Ala Leu
       1               5                   10
```

( 2 ) INFORMATION FOR SEQ ID NO:7:

( i ) SEQUENCE CHARACTERISTICS:
        ( A ) LENGTH: 1969 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:7:

```
CAGATCTCCG CGATGGACGC CACCACCGGC GACTTCACGG CGCTGCAGAA GGCGGTGAAG      60
CAGATGGCCA CCAAGGCGGG CACTGAGGGC CTGGTGCACG GCATCAAGAA CCCCGACGTG     120
CGCCAGCTGC TGACCGAGAT CTTCATGAAG GACCCGGAGC AGCAGGAGTT CATGCAGGCG     180
GTGCGCGAGG TGGCCGTCTC CCTGCAGCCC GTGTTCGAGA AGCGCCCCGA GCTGCTGCCC     240
ATCTTCAAGC AGATCGTTGA GCCTGAGCGC GTGATCACCT TCCGCGTGTC CTGGCTGGAC     300
GACGCCGGCA ACCTGCAGGT CAACCGCGGC TTCCGCGTGC AGTACTCGTC CGCCATCGGC     360
CCCTACAAGG GCGGCCTGCG CTTCCACCCC TCCGTGAACC TGTCCATCAT GAAGTTCCTT     420
GCCTTTGAGC AGATCTTCAA GAACAGCCTG ACCACCCTGC CCATGGGCGG CGGCAAGGGC     480
GGCTCCGACT TCGACCCCAA GGGCAAGAGC GACGCGGAGG TGATGCGCTT CTGCCAGTCC     540
TTCATGACCG AGCTGCAGCG CCACATCAGC TACGTGCAGG ACGTGCCCGC CGGCGACATC     600
GGCGTGGGCG CGCGCGAGAT TGGCTACCTT TTCGGCCAGT ACAAGCGCAT CACCAAGAAC     660
TACACCGGCG TGCTGACCCC GAAGGGCCAG GAGTATGGCG GCTCCGAGAT CCGCCCCGAG     720
GCCACCGGCT ACGGCGCCGT GCTGTTTGTG GAGAACGTGC TGAAGGACAA GGGCGAGAGC     780
CTCAAGGGCA AGCGCTGCCT GGTGTCTGGC GCGGGCAACG TGGCCCAGTA CTGCGCGGAG     840
CTGCTGCTGG AGAAGGGCGC CATCGTGCTG TCGCTGTCCG ACTCCCAGGG CTACGTGTAC     900
GAGCCCAACG GCTTCACGCG CGAGCAGCTG CAGGCGGTGC AGGACATGAA GAAGAAGAAC     960
AACAGCGCCC GCATCTCCGA GTACAAGAGC GACACCGCCG TGTATGTGGG CGACCGCCGC    1020
AAGCCTTGGG AGCTGGACTG CCAGGTGGAC ATCGCCTTCC CCTGCGCCAC CCAGAACGAG    1080
ATCGATGAGC ACGACGCCGA GCTGCTGATC AAGCACGGCT GCCAGTACGT GGTGGAGGGC    1140
GCCAACATGC CCTCCACCAA CGAGGCCATC CACAAGTACA ACAAGGCCGG CATCATCTAC    1200
TGCCCCGGCA AGGCGGCCAA CGCCGGCGGC GTGGCGGTCA GCGGCCTGGA GATGACCCAG    1260
AACCGCATGA GCCTGAACTG GACTCGCGAG GAGGTTCGCG ACAAGCTGGA GCGCATCATG    1320
AAGGACATCT ACGACTCCGC CATGGGGCCG TCCCGCAGAT ACAATGTTGA CCTGGCTGCG    1380
```

```
GGCGCCAACA  TCGCGGGCTT  CACCAAGGTG  GCTGATGCCG  TCAAGGCCCA  GGGCGCTGTT    1440

TAAGCTGCCC  AGGCCCAAGC  CACGGCTCAC  CGGCAATCCA  ACCCAACCAA  CTCAACGGCC    1500

AGGACCTTTT  CGGAAGCGGC  GCCTTTTTCC  CAGCCAGGGC  CCTCACCTGC  CCTTTCATAA    1560

CCCTGCTATT  GCCGCCGTGC  CCCTGCAATT  CCACCCCAAG  AAGAACTAGC  GGCACTTGAC    1620

TGCATCAGGA  CGGCTATTTT  TTTCGCGACG  CGCGCTCACC  CCGAGAGCCT  CTCTCCCCCG    1680

AGCCCTAAGC  GCTGACGTCC  GCCCGACTTT  GCCTCGCACA  TCGCTCGGTT  TTGACCCCCT    1740

CCAGTCTACC  CACCCTGTTG  TGAAGCCTAC  CAGCTCAATT  GCCTTTAGT   GTATGTGCGC    1800

CCCCTCCTGC  CCCCGAATTT  TCCTGCCATG  AGACGTGCGG  TTCCTAGCCT  GGTGACCCCA    1860

AGTAGCAGTT  AGTGTGCGTG  CCTTGCCCTG  CGCTGCCCGG  GATGCGATAC  TGTGACCTGA    1920

GAGTGCTTGT  GTAAACACGA  CGAGTCAAAA  AAAAAAAAAA  AAAAAAAA                  1969
```

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:8:

```
CTCAAAGGCA  AGGAACTTCA  TG                                                  22
```

(2) INFORMATION FOR SEQ ID NO:9:

(i) SEQUENCE CHARACTERISTICS:
        (A) LENGTH: 50 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:9:

```
GGGTCGACAT  TCTAGACAGA  ATTCGTGGAT  CCTTTTTTTT  TTTTTTTTT                   50
```

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:10:

```
GGACGAGTAC  TGCACGC                                                         17
```

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: CDNA (xi) SEQUENCE DESCRIPTION: SEQ ID NO:11:

```
GATCTCGGTC  AGCAGCTG                                                        18
```

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: CDNA ( x i ) SEQUENCE DESCRIPTION: SEQ ID NO:12:

```
GGGTCGACAT   TCTAGACAGA   A                                                                 21
```

( 2 ) INFORMATION FOR SEQ ID NO:13:

( i ) SEQUENCE CHARACTERISTICS:
        ( A ) LENGTH: 367 base pairs
        ( B ) TYPE: nucleic acid
        ( C ) STRANDEDNESS: double
        ( D ) TOPOLOGY: linear ( i i ) MOLECULE TYPE: CDNA ( x i ) SEQUENCE DESCRIPTION: SEQ ID NO:13:

```
GGGTCGACAT   TCTAGACAGA   ATTCGTGGAT   CCTTTTTTTT   TTTTTTTTTT   TTTTTCTCC      60
TTTCTGCTCG   CCCTCTCTCC   GTCCCGCCAT   GCAGACCGCC   CTCGTCGCCA   AGCCTATCGT    120
GGCCGCCCCG   CTGGCGGCAC   GCCCGCGCTG   CCTCGCGCCG   TGGCCGTGCG   CGTGGGTCCG    180
CTCCGCCAAG   CGCGATGTCC   GCGCCAAGGC   CGTCTCGCTG   GAGGAGCAGA   TCTCCGCGAT    240
GGACGCCACC   ACCGGCGACT   TCACGGCGCT   GCAGAAGGCG   GTGAAGCAGA   TGGCCACCAA    300
GGCGGGCACT   GAGGGCCTGG   TGCACGGCAT   CAAGAACCCC   GACGTGCGCC   AGCTGCTGAC    360
CGAGATC                                                                       367
```

( 2 ) INFORMATION FOR SEQ ID NO:14:

( i ) SEQUENCE CHARACTERISTICS:
        ( A ) LENGTH: 325 base pairs
        ( B ) TYPE: nucleic acid
        ( C ) STRANDEDNESS: double
        ( D ) TOPOLOGY: linear ( i i ) MOLECULE TYPE: CDNA ( x i ) SEQUENCE DESCRIPTION: SEQ ID NO:14:

```
GGGTCGACAT   TCTAGACAGA   ATTCGTGGAT   CCTTTTTTTT   TTTTTTTTTT   TTTTTCTCC      60
TTTCTGCTCG   CCCTCTCTCC   GTCCCGCCAT   GCAGACCGCC   CTCGTCGCCA   AGCCTATCGT    120
GGCCTGCGCG   TGGGTCCGCT   CCGCCAAGCG   CGATGTCCGC   GCCAAGGCCG   TCTCGCTGGA    180
GGAGCAGATC   TCCGCGATGG   ACGCCACCAC   CGGCGACTTC   ACGGCGCTGC   AGAAGGCGGT    240
GAAGCAGATG   GCCACCAAGG   CGGGCACTGA   GGGCCTGGTG   CACGGCATCA   AGAACCCCGA    300
CGTGCGCCAG   CTGCTGACCG   AGATC                                               325
```

( 2 ) INFORMATION FOR SEQ ID NO:15:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: CDNA ( x i ) SEQUENCE DESCRIPTION: SEQ ID NO:15:

-continued

CTTTCTGCTC GCCCTCTC                                                                                    18

( 2 ) INFORMATION FOR SEQ ID NO:16:

( i ) SEQUENCE CHARACTERISTICS:
          ( A ) LENGTH: 308 base pairs
          ( B ) TYPE: nucleic acid
          ( C ) STRANDEDNESS: double
          ( D ) TOPOLOGY: linear ( i i ) MOLECULE TYPE: cDNA ( x i ) SEQUENCE DESCRIPTION: SEQ ID NO:16:

CTTTCTGCTC GCCCTCTCTC CGTCCCGCCA TGCAGACCGC CCTCGTCGCC AAGCCTATCG        60

TGGCCGCCCC GCTGGCGGCA CGCCCGCGCT GCCTCGCGCC GTGGCCGTGC GCGTGGGTCC       120

GCTCCGCCAA GCGCGATGTC CGCGCCAAGG CCGTCTCGCT GGAGGAGCAG ATCTCCGCGA       180

TGGACGCCAC CACCGGCGAC TTCACGGCGC TGCAGAAGGC GGTGAAGCAG ATGGCCACCA       240

AGGCGGGCAC TGAGGGCCTG GTGCACGGCA TCAAGAACCC CGACGTGCGC CAGCTGCTGA       300

CCGAGATC                                                               308

( 2 ) INFORMATION FOR SEQ ID NO:17:

( i ) SEQUENCE CHARACTERISTICS:
          ( A ) LENGTH: 266 base pairs
          ( B ) TYPE: nucleic acid
          ( C ) STRANDEDNESS: double
          ( D ) TOPOLOGY: linear ( i i ) MOLECULE TYPE: cDNA ( x i ) SEQUENCE DESCRIPTION: SEQ ID NO:17:

CTTTCTGCTC GCCCTCTCTC CGTCCCGCCA TGCAGACCGC CCTCGTCGCC AAGCCTATCG        60

TGGCCTGCGC GTGGGTCCGC TCCGCCAAGC GCGATGTCCG CGCCAAGGCC GTCTCGCTGG       120

AGGAGCAGAT CTCCGCGATG GACGCCACCA CCGGCGACTT CACGGCGCTG CAGAAGGCGG       180

TGAAGCAGAT GGCCACCAAG GCGGGCACTG AGGGCCTGGT GCACGGCATC AAGAACCCCG       240

ACGTGCGCCA GCTGCTGACC GAGATC                                           266

( 2 ) INFORMATION FOR SEQ ID NO:18:

( i ) SEQUENCE CHARACTERISTICS:
          ( A ) LENGTH: 2137 base pairs
          ( B ) TYPE: nucleic acid
          ( C ) STRANDEDNESS: double
          ( D ) TOPOLOGY: linear ( i i ) MOLECULE TYPE: cDNA ( x i ) SEQUENCE DESCRIPTION: SEQ ID NO:18:

CTTTCTGCTC GCCCTCTCTC CGTCCCGCCA TGCAGACCGC CCTCGTCGCC AAGCCTATCG        60

TGGCCGCCCC GCTGGCGGCA CGCCCGCGCT GCCTCGCGCC GTGGCCGTGC GCGTGGGTCC       120

GCTCCGCCAA GCGCGATGTC CGCGCCAAGG CCGTCTCGCT GGAGGAGCAG ATCTCCGCGA       180

TGGACGCCAC CACCGGCGAC TTCACGGCGC TGCAGAAGGC GGTGAAGCAG ATGGCCACCA       240

AGGCGGGCAC TGAGGGCCTG GTGCACGGCA TCAAGAACCC CGACGTGCGC CAGCTGCTGA       300

CCGAGATCTT CATGAAGGAC CCGGAGCAGC AGGAGTTCAT GCAGGCGGTG CGCGAGGTGG       360

CCGTCTCCCT GCAGCCCGTG TTCGAGAAGC GCCCCGAGCT GCTGCCCATC TTCAAGCAGA       420

TCGTTGAGCC TGAGCGCGTG ATCACCTTCC GCGTGTCCTG GCTGGACGAC GCCGGCAACC       480

| | | | | | |
|---|---|---|---|---|---|
| TGCAGGTCAA | CCGCGGCTTC | CGCGTGCAGT | ACTCGTCCGC | CATCGGCCCC | TACAAGGGCG | 540
| GCCTGCGCTT | CCACCCCTCC | GTGAACCTGT | CCATCATGAA | GTTCCTTGCC | TTTGAGCAGA | 600
| TCTTCAAGAA | CAGCCTGACC | ACCCTGCCCA | TGGGCGGCGG | CAAGGGCGGC | TCCGACTTCG | 660
| ACCCCAAGGG | CAAGAGCGAC | GCGGAGGTGA | TGCGCTTCTG | CCAGTCCTTC | ATGACCGAGC | 720
| TGCAGCGCCA | CATCAGCTAC | GTGCAGGACG | TGCCCGCCGG | CGACATCGGC | GTGGGCGCGC | 780
| GCGAGATTGG | CTACCTTTTC | GGCCAGTACA | AGCGCATCAC | CAAGAACTAC | ACCGGCGTGC | 840
| TGACCCCGAA | GGGCCAGGAG | TATGGCGGCT | CCGAGATCCG | CCCCGAGGCC | ACCGGCTACG | 900
| GCGCCGTGCT | GTTTGTGGAG | AACGTGCTGA | AGGACAAGGG | CGAGAGCCTC | AAGGGCAAGC | 960
| GCTGCCTGGT | GTCTGGCGCG | GGCAACGTGG | CCCAGTACTG | CGCGGAGCTG | CTGCTGGAGA | 1020
| AGGGCGCCAT | CGTGCTGTCG | CTGTCCGACT | CCCAGGGCTA | CGTGTACGAG | CCCAACGGCT | 1080
| TCACGCGCGA | GCAGCTGCAG | GCGGTGCAGG | ACATGAAGAA | GAAGAACAAC | AGCGCCCGCA | 1140
| TCTCCGAGTA | CAAGAGCGAC | ACCGCCGTGT | ATGTGGGCGA | CCGCCGCAAG | CCTTGGGAGC | 1200
| TGGACTGCCA | GGTGGACATC | GCCTTCCCCT | GCGCCACCCA | GAACGAGATC | GATGAGCACG | 1260
| ACGCCGAGCT | GCTGATCAAG | CACGGCTGCC | AGTACGTGGT | GGAGGGCGCC | AACATGCCCT | 1320
| CCACCAACGA | GGCCATCCAC | AAGTACAACA | AGGCCGGCAT | CATCTACTGC | CCCGGCAAGG | 1380
| CGGCCAACGC | CGGCGGCGTG | GCGGTCAGCG | GCCTGGAGAT | GACCCAGAAC | CGCATGAGCC | 1440
| TGAACTGGAC | TCGCGAGGAG | GTTCGCGACA | AGCTGGAGCG | CATCATGAAG | GACATCTACG | 1500
| ACTCCGCCAT | GGGGCCGTCC | CGCAGATACA | ATGTTGACCT | GGCTGCGGGC | GCCAACATCG | 1560
| CGGGCTTCAC | CAAGGTGGCT | GATGCCGTCA | AGGCCCAGGG | CGCTGTTTAA | GCTGCCCAGG | 1620
| CCCAAGCCAC | GGCTCACCGG | CAATCCAACC | CAACCAACTC | AACGGCCAGG | ACCTTTTCGG | 1680
| AAGCGGCGCC | TTTTTCCCAG | CCAGGGCCCT | CACCTGCCCT | TTCATAACCC | TGCTATTGCC | 1740
| GCCGTGCCCC | TGCAATTCCA | CCCCAAGAAG | AACTAGCGGC | ACTTGACTGC | ATCAGGACGG | 1800
| CTATTTTTTT | CGCGACGCGC | GCTCACCCCG | AGAGCCTCTC | TCCCCCGAGC | CCTAAGCGCT | 1860
| GACGTCCGCC | CGACTTTGCC | TCGCACATCG | CTCGGTTTTG | ACCCCTCCA | GTCTACCCAC | 1920
| CCTGTTGTGA | AGCCTACCAG | CTCAATTGCC | TTTTAGTGTA | TGTGCGCCCC | CTCCTGCCCC | 1980
| CGAATTTTCC | TGCCATGAGA | CGTGCGGTTC | CTAGCCTGGT | GACCCCAAGT | AGCAGTTAGT | 2040
| GTGCGTGCCT | TGCCCTGCGC | TGCCCGGGAT | GCGATACTGT | GACCTGAGAG | TGCTTGTGTA | 2100
| AACACGACGA | GTCAAAAAAA | AAAAAAAAA | AAAAAA | | | 2137

( 2 ) INFORMATION FOR SEQ ID NO:19:

( i ) SEQUENCE CHARACTERISTICS:
        ( A ) LENGTH: 2096 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:19:

| | | | | | |
|---|---|---|---|---|---|
| CTTTCTGCTC | GCCCTCTCTC | CGTCCCGCCA | TGCAGACCGC | CCTCGTCGCC | AAGCCTATCG | 60
| TGGCCTGCGC | GTGGGTCCGC | TCCGCCAAGC | GCGATGTCCG | CGCCAAGGCC | GTCTCGCTGG | 120
| AGGAGCAGAT | CTCCGCGATG | GACGCCACCA | CCGGCGACTT | CACGGCGCTG | CAGAAGGCGG | 180
| TGAAGCAGAT | GGCCACCAAG | GCGGGCACTG | AGGGCCTGGT | GCACGGCATC | AAGAACCCCG | 240
| ACGTGCGCCA | GCTGCTGACC | GAGATCTTCA | TGAAGGACCC | GGAGCAGCAG | GAGTTCATGC | 300
| AGGCGGTGCG | CGAGGTGGCC | GTCTCCCTGC | AGCCCGTGTT | CGAGAAGCGC | CCCGAGCTGC | 360

| | | | | | | |
|---|---|---|---|---|---|---|
| TGCCCATCTT | CAAGCAGATC | GTTGAGCCTG | AGCGCGTGAT | CACCTTCCGC | GTGTCCTGGC | 420 |
| TGGACGACGC | CGGCAACCTG | CAGGTCAACC | GCGGCTTCCG | CGTGCAGTAC | TCGTCCGCCA | 480 |
| TCGGCCCCTA | CAAGGGCGGC | CTGCGCTTCC | ACCCTCCGT | GAACCTGTCC | ATCATGAAGT | 540 |
| TCCTTGCCTT | TGAGCAGATC | TTCAAGAACA | GCCTGACCAC | CCTGCCCATG | GGCGGCGGCA | 600 |
| AGGGCGGCTC | CGACTTCGAC | CCCAAGGGCA | AGAGCGACGC | GGAGGTGATG | CGCTTCTGCC | 660 |
| AGTCCTTCAT | GACCGAGCTG | CAGCGCCACA | TCAGCTACGT | GCAGGACGTG | CCCGCCGGCG | 720 |
| ACATCGGCGT | GGGCGCGCGC | GAGATTGGCT | ACCTTTTCGG | CCAGTACAAG | CGCATCACCA | 780 |
| AGAACTACAC | CGGCGTGCTG | ACCCCGAAGG | GCCAGGAGTA | TGGCGGCTCC | GAGATCCGCC | 840 |
| CCGAGGCCAC | CGGCTACGGC | GCCGTGCTGT | TTGTGGAGAA | CGTGCTGAAG | GACAAGGGCG | 900 |
| AGAGCCTCAA | GGGCAAGCGC | TGCCTGGTGT | CTGGCGCGGG | CAACGTGGCC | CAGTACTGCG | 960 |
| CGGAGCTGCT | GCTGGAGAAG | GGCGCCATCG | TGCTGTCGCT | GTCCGACTCC | CAGGGCTACG | 1020 |
| TGTACGAGCC | CAACGGCTTC | ACGCGCGAGC | AGCTGCAGGC | GGTGCAGGAC | ATGAAGAAGA | 1080 |
| AGAACAACAG | CGCCCGCATC | TCCGAGTACA | AGAGCGACAC | CGCCGTGTAT | GTGGGCGACC | 1140 |
| GCCGCAAGCC | TTGGGAGCTG | GACTGCCAGG | TGGACATCGC | CTTCCCTGC | GCCACCCAGA | 1200 |
| ACGAGATCGA | TGAGCACGAC | GCCGAGCTGC | TGATCAAGCA | CGGCTGCCAG | TACGTGGTGG | 1260 |
| AGGGCGCCAA | CATGCCCTCC | ACCAACGAGG | CCATCCACAA | GTACAACAAG | GCCGGCATCA | 1320 |
| TCTACTGCCC | CGGCAAGGCG | GCCAACGCCG | GCGGCGTGGC | GGTCAGCGGC | CTGGAGATGA | 1380 |
| CCCAGAACCG | CATGAGCCTG | AACTGGACTC | GCGAGGAGGT | TCGCGACAAG | CTGGAGCGCA | 1440 |
| TCATGAAGGA | CATCTACGAC | TCCGCCATGG | GGCCGTCCCG | CAGATACAAT | GTTGACCTGG | 1500 |
| CTGCGGGCGC | CAACATCGCG | GGCTTCACCA | AGGTGGCTGA | TGCCGTCAAG | GCCCAGGGCG | 1560 |
| CTGTTTAAGC | TGCCCAGGCC | CAAGCACGG | CTCACCGGCA | ATCCAACCCA | ACCAACTCAA | 1620 |
| CGGCCAGGAC | CTTTTCGGAA | GCGGCGCCTT | TTTCCCAGCC | AGGGCCCTCA | CCTGCCCTTT | 1680 |
| CATAACCCTG | CTATTGCCGC | CGTGCCCCTG | CAATTCCACC | CCAAGAAGAA | CTAGCGGCAC | 1740 |
| TTGACTGCAT | CAGGACGGCT | ATTTTTTCG | CGACGCGCGC | TCACCCCGAG | AGCCTCTCTC | 1800 |
| CCCCGAGCCC | TAAGCGCTGA | CGTCCGCCCG | ACTTTGCCTC | GCACATCGCT | CGGTTTTGAC | 1860 |
| CCCCTCCAGT | CTACCCACCC | TGTTGTGAAG | CCTACCAGCT | CAATTGCCTT | TTAGTGTATG | 1920 |
| TGCGCCCCCT | CCTGCCCCCG | AATTTTCCTG | CCATGAGACG | TGCGGTTCCT | AGCCTGGTGA | 1980 |
| CCCCAAGTAG | CAGTTAGTGT | GCGTGCCTTG | CCCTGCGCTG | CCCGGGATGC | GATACTGTGA | 2040 |
| CCTGAGAGTG | CTTGTGTAAA | CACGACGAGT | CAAAAAAAAA | AAAAAAAAA | AAAAAA | 2096 |

( 2 ) INFORMATION FOR SEQ ID NO:20:

( i ) SEQUENCE CHARACTERISTICS:
        ( A ) LENGTH: 25 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:20:

CATATGGCCG TCTCGCTGGG AGGAG        25

( 2 ) INFORMATION FOR SEQ ID NO:21:

( i ) SEQUENCE CHARACTERISTICS:
        ( A ) LENGTH: 19 base pairs
        ( B ) TYPE: nucleic acid (C) STRANDEDNESS: double
(D) TOPOLOGY: linear (i i) MOLECULE TYPE: CDNA (x i) SEQUENCE DESCRIPTION: SEQ ID NO:21:

GTTGGATTGC CGGTGAGCC  19

(2) INFORMATION FOR SEQ ID NO:22:

(i) SEQUENCE CHARACTERISTICS:
(A) LENGTH: 21 base pairs
(B) TYPE: nucleic acid
(C) STRANDEDNESS: double
(D) TOPOLOGY: linear (i i) MOLECULE TYPE: CDNA (x i) SEQUENCE DESCRIPTION: SEQ ID NO:22:

CATATGGACG CCACCACCGG C  21

(2) INFORMATION FOR SEQ ID NO:23:

(i) SEQUENCE CHARACTERISTICS:
(A) LENGTH: 1506 base pairs
(B) TYPE: nucleic acid
(C) STRANDEDNESS: double
(D) TOPOLOGY: linear (i i) MOLECULE TYPE: CDNA (i x) FEATURE:
(A) NAME/KEY: CDS
(B) LOCATION: 4..1464

(x i) SEQUENCE DESCRIPTION: SEQ ID NO:23:

| CAT | ATG | GCC | GTC | TCG | CTG | GAG | GAG | CAG | ATC | TCC | GCG | ATG | GAC | GCC | ACC | 48 |
|---|---|---|---|---|---|---|---|---|---|---|---|---|---|---|---|---|
|  | Met | Ala | Val | Ser | Leu | Glu | Glu | Gln | Ile | Ser | Ala | Met | Asp | Ala | Thr |  |
|  |  |  | 515 |  |  |  | 520 |  |  |  |  | 525 |  |  |  |  |

| ACC | GGC | GAC | TTC | ACG | GCG | CTG | CAG | AAG | GCG | GTG | AAG | CAG | ATG | GCC | ACC | 96 |
|---|---|---|---|---|---|---|---|---|---|---|---|---|---|---|---|---|
| Thr | Gly | Asp | Phe | Thr | Ala | Leu | Gln | Lys | Ala | Val | Lys | Gln | Met | Ala | Thr |  |
|  |  | 530 |  |  |  |  | 535 |  |  |  |  | 540 |  |  |  |  |

| AAG | GCG | GGC | ACT | GAG | GGC | CTG | GTG | CAC | GGC | ATC | AAG | AAC | CCC | GAC | GTG | 144 |
|---|---|---|---|---|---|---|---|---|---|---|---|---|---|---|---|---|
| Lys | Ala | Gly | Thr | Glu | Gly | Leu | Val | His | Gly | Ile | Lys | Asn | Pro | Asp | Val |  |
| 545 |  |  |  |  | 550 |  |  |  |  | 555 |  |  |  |  |  |  |

| CGC | CAG | CTG | CTG | ACC | GAG | ATC | TTC | ATG | AAG | GAC | CCG | GAG | CAG | CAG | GAG | 192 |
|---|---|---|---|---|---|---|---|---|---|---|---|---|---|---|---|---|
| Arg | Gln | Leu | Leu | Thr | Glu | Ile | Phe | Met | Lys | Asp | Pro | Glu | Gln | Gln | Glu |  |
| 560 |  |  |  |  | 565 |  |  |  |  | 570 |  |  |  |  | 575 |  |

| TTC | ATG | CAG | GCG | GTG | CGC | GAG | GTG | GCC | GTC | TCC | CTG | CAG | CCC | GTG | TTC | 240 |
|---|---|---|---|---|---|---|---|---|---|---|---|---|---|---|---|---|
| Phe | Met | Gln | Ala | Val | Arg | Glu | Val | Ala | Val | Ser | Leu | Gln | Pro | Val | Phe |  |
|  |  |  |  | 580 |  |  |  |  | 585 |  |  |  |  | 590 |  |  |

| GAG | AAG | CGC | CCC | GAG | CTG | CTG | CCC | ATC | TTC | AAG | CAG | ATC | GTT | GAG | CCT | 288 |
|---|---|---|---|---|---|---|---|---|---|---|---|---|---|---|---|---|
| Glu | Lys | Arg | Pro | Glu | Leu | Leu | Pro | Ile | Phe | Lys | Gln | Ile | Val | Glu | Pro |  |
|  |  |  | 595 |  |  |  |  | 600 |  |  |  |  | 605 |  |  |  |

| GAG | CGC | GTG | ATC | ACC | TTC | CGC | GTG | TCC | TGG | CTG | GAC | GAC | GCC | GGC | AAC | 336 |
|---|---|---|---|---|---|---|---|---|---|---|---|---|---|---|---|---|
| Glu | Arg | Val | Ile | Thr | Phe | Arg | Val | Ser | Trp | Leu | Asp | Asp | Ala | Gly | Asn |  |
|  |  | 610 |  |  |  |  | 615 |  |  |  |  | 620 |  |  |  |  |

| CTG | CAG | GTC | AAC | CGC | GGC | TTC | CGC | GTG | CAG | TAC | TCG | TCC | GCC | ATC | GGC | 384 |
|---|---|---|---|---|---|---|---|---|---|---|---|---|---|---|---|---|
| Leu | Gln | Val | Asn | Arg | Gly | Phe | Arg | Val | Gln | Tyr | Ser | Ser | Ala | Ile | Gly |  |
|  | 625 |  |  |  |  | 630 |  |  |  |  | 635 |  |  |  |  |  |

| CCC | TAC | AAG | GGC | GGC | CTG | CGC | TTC | CAC | CCC | TCC | GTG | AAC | CTG | TCC | ATC | 432 |
|---|---|---|---|---|---|---|---|---|---|---|---|---|---|---|---|---|
| Pro | Tyr | Lys | Gly | Gly | Leu | Arg | Phe | His | Pro | Ser | Val | Asn | Leu | Ser | Ile |  |
| 640 |  |  |  |  | 645 |  |  |  |  | 650 |  |  |  |  | 655 |  |

| ATG | AAG | TTC | CTT | GCC | TTT | GAG | CAG | ATC | TTC | AAG | AAC | AGC | CTG | ACC | ACC | 480 |
|---|---|---|---|---|---|---|---|---|---|---|---|---|---|---|---|---|
| Met | Lys | Phe | Leu | Ala | Phe | Glu | Gln | Ile | Phe | Lys | Asn | Ser | Leu | Thr | Thr |  |
|  |  |  |  | 660 |  |  |  |  | 665 |  |  |  |  | 670 |  |  |

| | | | | | | | | | | | | | | | | |
|---|---|---|---|---|---|---|---|---|---|---|---|---|---|---|---|---|
| CTG | CCC | ATG | GGC | GGC | GGC | AAG | GGC | GGC | TCC | GAC | TTC | GAC | CCC | AAG | GGC | 528 |
| Leu | Pro | Met | Gly | Gly | Gly | Lys | Gly | Gly | Ser | Asp | Phe | Asp | Pro | Lys | Gly | |
| | | | 675 | | | | 680 | | | | | | 685 | | | |
| AAG | AGC | GAC | GCG | GAG | GTG | ATG | CGC | TTC | TGC | CAG | TCC | TTC | ATG | ACC | GAG | 576 |
| Lys | Ser | Asp | Ala | Glu | Val | Met | Arg | Phe | Cys | Gln | Ser | Phe | Met | Thr | Glu | |
| | | 690 | | | | | 695 | | | | | 700 | | | | |
| CTG | CAG | CGC | CAC | ATC | AGC | TAC | GTG | CAG | GAC | GTG | CCC | GCC | GGC | GAC | ATC | 624 |
| Leu | Gln | Arg | His | Ile | Ser | Tyr | Val | Gln | Asp | Val | Pro | Ala | Gly | Asp | Ile | |
| | 705 | | | | | 710 | | | | | 715 | | | | | |
| GGC | GTG | GGC | GCG | CGC | GAG | ATT | GGC | TAC | CTT | TTC | GGC | CAG | TAC | AAG | CGC | 672 |
| Gly | Val | Gly | Ala | Arg | Glu | Ile | Gly | Tyr | Leu | Phe | Gly | Gln | Tyr | Lys | Arg | |
| 720 | | | | | 725 | | | | | 730 | | | | | 735 | |
| ATC | ACC | AAG | AAC | TAC | ACC | GGC | GTG | CTG | ACC | CCG | AAG | GGC | CAG | GAG | TAT | 720 |
| Ile | Thr | Lys | Asn | Tyr | Thr | Gly | Val | Leu | Thr | Pro | Lys | Gly | Gln | Glu | Tyr | |
| | | | | 740 | | | | | 745 | | | | | 750 | | |
| GGC | GGC | TCC | GAG | ATC | CGC | CCC | GAG | GCC | ACC | GGC | TAC | GGC | GCC | GTG | CTG | 768 |
| Gly | Gly | Ser | Glu | Ile | Arg | Pro | Glu | Ala | Thr | Gly | Tyr | Gly | Ala | Val | Leu | |
| | | | 755 | | | | | 760 | | | | | 765 | | | |
| TTT | GTG | GAG | AAC | GTG | CTG | AAG | GAC | AAG | GGC | GAG | AGC | CTC | AAG | GGC | AAG | 816 |
| Phe | Val | Glu | Asn | Val | Leu | Lys | Asp | Lys | Gly | Glu | Ser | Leu | Lys | Gly | Lys | |
| | | 770 | | | | | 775 | | | | | 780 | | | | |
| CGC | TGC | CTG | GTG | TCT | GGC | GCG | GGC | AAC | GTG | GCC | CAG | TAC | TGC | GCG | GAG | 864 |
| Arg | Cys | Leu | Val | Ser | Gly | Ala | Gly | Asn | Val | Ala | Gln | Tyr | Cys | Ala | Glu | |
| | 785 | | | | | 790 | | | | | 795 | | | | | |
| CTG | CTG | CTG | GAG | AAG | GGC | GCC | ATC | GTG | CTG | TCG | CTG | TCC | GAC | TCC | CAG | 912 |
| Leu | Leu | Leu | Glu | Lys | Gly | Ala | Ile | Val | Leu | Ser | Leu | Ser | Asp | Ser | Gln | |
| 800 | | | | | 805 | | | | | 810 | | | | | 815 | |
| GGC | TAC | GTG | TAC | GAG | CCC | AAC | GGC | TTC | ACG | CGC | GAG | CAG | CTG | CAG | GCG | 960 |
| Gly | Tyr | Val | Tyr | Glu | Pro | Asn | Gly | Phe | Thr | Arg | Glu | Gln | Leu | Gln | Ala | |
| | | | | 820 | | | | | 825 | | | | | 830 | | |
| GTG | CAG | GAC | ATG | AAG | AAG | AAG | AAC | AAC | AGC | GCC | CGC | ATC | TCC | GAG | TAC | 1008 |
| Val | Gln | Asp | Met | Lys | Lys | Lys | Asn | Asn | Ser | Ala | Arg | Ile | Ser | Glu | Tyr | |
| | | | 835 | | | | | 840 | | | | | 845 | | | |
| AAG | AGC | GAC | ACC | GCC | GTG | TAT | GTG | GGC | GAC | CGC | CGC | AAG | CCT | TGG | GAG | 1056 |
| Lys | Ser | Asp | Thr | Ala | Val | Tyr | Val | Gly | Asp | Arg | Arg | Lys | Pro | Trp | Glu | |
| | | 850 | | | | | 855 | | | | | 860 | | | | |
| CTG | GAC | TGC | CAG | GTG | GAC | ATC | GCC | TTC | CCC | TGC | GCC | ACC | CAG | AAC | GAG | 1104 |
| Leu | Asp | Cys | Gln | Val | Asp | Ile | Ala | Phe | Pro | Cys | Ala | Thr | Gln | Asn | Glu | |
| | 865 | | | | | 870 | | | | | 875 | | | | | |
| ATC | GAT | GAG | CAC | GAC | GCC | GAG | CTG | CTG | ATC | AAG | CAC | GGC | TGC | CAG | TAC | 1152 |
| Ile | Asp | Glu | His | Asp | Ala | Glu | Leu | Leu | Ile | Lys | His | Gly | Cys | Gln | Tyr | |
| 880 | | | | | 885 | | | | | 890 | | | | | 895 | |
| GTG | GTG | GAG | GGC | GCC | AAC | ATG | CCC | TCC | ACC | AAC | GAG | GCC | ATC | CAC | AAG | 1200 |
| Val | Val | Glu | Gly | Ala | Asn | Met | Pro | Ser | Thr | Asn | Glu | Ala | Ile | His | Lys | |
| | | | | 900 | | | | | 905 | | | | | 910 | | |
| TAC | AAC | AAG | GCC | GGC | ATC | ATC | TAC | TGC | CCC | GGC | AAG | GCG | GCC | AAC | GCC | 1248 |
| Tyr | Asn | Lys | Ala | Gly | Ile | Ile | Tyr | Cys | Pro | Gly | Lys | Ala | Ala | Asn | Ala | |
| | | | 915 | | | | | 920 | | | | | 925 | | | |
| GGC | GGC | GTG | GCG | GTC | AGC | GGC | CTG | GAG | ATG | ACC | CAG | AAC | CGC | ATG | AGC | 1296 |
| Gly | Gly | Val | Ala | Val | Ser | Gly | Leu | Glu | Met | Thr | Gln | Asn | Arg | Met | Ser | |
| | | 930 | | | | | 935 | | | | | 940 | | | | |
| CTG | AAC | TGG | ACT | CGC | GAG | GAG | GTT | CGC | GAC | AAG | CTG | GAG | CGC | ATC | ATG | 1344 |
| Leu | Asn | Trp | Thr | Arg | Glu | Glu | Val | Arg | Asp | Lys | Leu | Glu | Arg | Ile | Met | |
| | 945 | | | | | 950 | | | | | 955 | | | | | |
| AAG | GAC | ATC | TAC | GAC | TCC | GCC | ATG | GGG | CCG | TCC | CGC | AGA | TAC | AAT | GTT | 1392 |
| Lys | Asp | Ile | Tyr | Asp | Ser | Ala | Met | Gly | Pro | Ser | Arg | Arg | Tyr | Asn | Val | |
| 960 | | | | | 965 | | | | | 970 | | | | | 975 | |
| GAC | CTG | GCT | GCG | GGC | GCC | AAC | ATC | GCG | GGC | TTC | ACC | AAG | GTG | GCT | GAT | 1440 |
| Asp | Leu | Ala | Ala | Gly | Ala | Asn | Ile | Ala | Gly | Phe | Thr | Lys | Val | Ala | Asp | |
| | | | | 980 | | | | | 985 | | | | | 990 | | |

```
GCC GTC AAG GCC CAG GGC GCT GTT TAAGCTGCCC AGGCCCAAGC CACGGCTCAC    1494
Ala Val Lys Ala Gln Gly Ala Val
            995

CGGCAATCCA AC                                                        1506
```

( 2 ) INFORMATION FOR SEQ ID NO:24:

( i ) SEQUENCE CHARACTERISTICS:
        ( A ) LENGTH: 487 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

```
Met Ala Val Ser Leu Glu Glu Gln Ile Ser Ala Met Asp Ala Thr Thr
 1               5                  10                  15

Gly Asp Phe Thr Ala Leu Gln Lys Ala Val Lys Gln Met Ala Thr Lys
                20                  25                  30

Ala Gly Thr Glu Gly Leu Val His Gly Ile Lys Asn Pro Asp Val Arg
            35                  40                  45

Gln Leu Leu Thr Glu Ile Phe Met Lys Asp Pro Glu Gln Gln Glu Phe
    50                  55                  60

Met Gln Ala Val Arg Val Ala Val Ser Leu Pro Val Phe Glu
65                  70                  75              80

Lys Arg Pro Glu Leu Leu Pro Ile Phe Lys Gln Ile Val Glu Pro Glu
                85                  90                  95

Arg Val Ile Thr Phe Arg Val Ser Trp Leu Asp Asp Ala Gly Asn Leu
            100                 105                 110

Gln Val Asn Arg Gly Phe Arg Val Gln Tyr Ser Ser Ala Ile Gly Pro
            115                 120                 125

Tyr Lys Gly Gly Leu Arg Phe His Pro Ser Val Asn Leu Ser Ile Met
    130                 135                 140

Lys Phe Leu Ala Phe Glu Gln Ile Phe Lys Asn Ser Leu Thr Thr Leu
145                 150                 155                 160

Pro Met Gly Gly Gly Lys Gly Gly Ser Asp Phe Asp Pro Lys Gly Lys
                165                 170                 175

Ser Asp Ala Glu Val Met Arg Phe Cys Gln Ser Phe Met Thr Glu Leu
            180                 185                 190

Gln Arg His Ile Ser Tyr Val Gln Asp Val Pro Ala Gly Asp Ile Gly
            195                 200                 205

Val Gly Ala Arg Glu Ile Gly Tyr Leu Phe Gly Gln Tyr Lys Arg Ile
    210                 215                 220

Thr Lys Asn Tyr Thr Gly Val Leu Thr Pro Lys Gly Gln Glu Tyr Gly
225                 230                 235                 240

Gly Ser Glu Ile Arg Pro Glu Ala Thr Gly Tyr Gly Ala Val Leu Phe
                245                 250                 255

Val Glu Asn Val Leu Lys Asp Lys Gly Glu Ser Leu Lys Gly Lys Arg
            260                 265                 270

Cys Leu Val Ser Gly Ala Gly Asn Val Ala Gln Tyr Cys Ala Glu Leu
            275                 280                 285

Leu Leu Glu Lys Gly Ala Ile Val Leu Ser Leu Ser Asp Ser Gln Gly
    290                 295                 300

Tyr Val Tyr Glu Pro Asn Gly Phe Thr Arg Glu Gln Leu Gln Ala Val
305                 310                 315                 320
```

| Gln | Asp | Met | Lys | Lys | Lys | Asn | Asn | Ser | Ala | Arg | Ile | Ser | Glu | Tyr | Lys |
|---|---|---|---|---|---|---|---|---|---|---|---|---|---|---|---|
|  |  |  |  | 325 |  |  |  |  | 330 |  |  |  |  | 335 |  |

| Ser | Asp | Thr | Ala | Val | Tyr | Val | Gly | Asp | Arg | Arg | Lys | Pro | Trp | Glu | Leu |
|---|---|---|---|---|---|---|---|---|---|---|---|---|---|---|---|
|  |  |  | 340 |  |  |  |  | 345 |  |  |  | 350 |  |  |  |

| Asp | Cys | Gln | Val | Asp | Ile | Ala | Phe | Pro | Cys | Ala | Thr | Gln | Asn | Glu | Ile |
|---|---|---|---|---|---|---|---|---|---|---|---|---|---|---|---|
|  |  | 355 |  |  |  |  | 360 |  |  |  |  | 365 |  |  |  |

| Asp | Glu | His | Asp | Ala | Glu | Leu | Leu | Ile | Lys | His | Gly | Cys | Gln | Tyr | Val |
|---|---|---|---|---|---|---|---|---|---|---|---|---|---|---|---|
| 370 |  |  |  |  |  | 375 |  |  |  |  | 380 |  |  |  |  |

| Val | Glu | Gly | Ala | Asn | Met | Pro | Ser | Thr | Asn | Glu | Ala | Ile | His | Lys | Tyr |
|---|---|---|---|---|---|---|---|---|---|---|---|---|---|---|---|
| 385 |  |  |  |  | 390 |  |  |  |  | 395 |  |  |  |  | 400 |

| Asn | Lys | Ala | Gly | Ile | Ile | Tyr | Cys | Pro | Gly | Lys | Ala | Ala | Asn | Ala | Gly |
|---|---|---|---|---|---|---|---|---|---|---|---|---|---|---|---|
|  |  |  |  | 405 |  |  |  |  | 410 |  |  |  |  | 415 |  |

| Gly | Val | Ala | Val | Ser | Gly | Leu | Glu | Met | Thr | Gln | Asn | Arg | Met | Ser | Leu |
|---|---|---|---|---|---|---|---|---|---|---|---|---|---|---|---|
|  |  |  | 420 |  |  |  |  | 425 |  |  |  |  | 430 |  |  |

| Asn | Trp | Thr | Arg | Glu | Glu | Val | Arg | Asp | Lys | Leu | Glu | Arg | Ile | Met | Lys |
|---|---|---|---|---|---|---|---|---|---|---|---|---|---|---|---|
|  |  | 435 |  |  |  |  | 440 |  |  |  |  | 445 |  |  |  |

| Asp | Ile | Tyr | Asp | Ser | Ala | Met | Gly | Pro | Ser | Arg | Arg | Tyr | Asn | Val | Asp |
|---|---|---|---|---|---|---|---|---|---|---|---|---|---|---|---|
|  | 450 |  |  |  |  | 455 |  |  |  |  | 460 |  |  |  |  |

| Leu | Ala | Ala | Gly | Ala | Asn | Ile | Ala | Gly | Phe | Thr | Lys | Val | Ala | Asp | Ala |
|---|---|---|---|---|---|---|---|---|---|---|---|---|---|---|---|
| 465 |  |  |  |  | 470 |  |  |  |  | 475 |  |  |  |  | 480 |

| Val | Lys | Ala | Gln | Gly | Ala | Val |
|---|---|---|---|---|---|---|
|  |  |  |  | 485 |  |  |

(2) INFORMATION FOR SEQ ID NO:25:

(i) SEQUENCE CHARACTERISTICS:
        (A) LENGTH: 1473 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 4..1431

(xi) SEQUENCE DESCRIPTION: SEQ ID NO:25:

| CAT | ATG | GAC | GCC | ACC | ACC | GGC | GAC | TTC | ACG | GCG | CTG | CAG | AAG | GCG | GTG | 48 |
|---|---|---|---|---|---|---|---|---|---|---|---|---|---|---|---|---|
|  | Met | Asp | Ala | Thr | Thr | Gly | Asp | Phe | Thr | Ala | Leu | Gln | Lys | Ala | Val |  |
|  |  |  | 490 |  |  |  |  | 495 |  |  |  |  | 500 |  |  |  |

| AAG | CAG | ATG | GCC | ACC | AAG | GCG | GGC | ACT | GAG | GGC | CTG | GTG | CAC | GGC | ATC | 96 |
|---|---|---|---|---|---|---|---|---|---|---|---|---|---|---|---|---|
| Lys | Gln | Met | Ala | Thr | Lys | Ala | Gly | Thr | Glu | Gly | Leu | Val | His | Gly | Ile |  |
|  |  | 505 |  |  |  |  | 510 |  |  |  |  | 515 |  |  |  |  |

| AAG | AAC | CCC | GAC | GTG | CGC | CAG | CTG | CTG | ACC | GAG | ATC | TTC | ATG | AAG | GAC | 144 |
|---|---|---|---|---|---|---|---|---|---|---|---|---|---|---|---|---|
| Lys | Asn | Pro | Asp | Val | Arg | Gln | Leu | Leu | Thr | Glu | Ile | Phe | Met | Lys | Asp |  |
|  | 520 |  |  |  |  | 525 |  |  |  |  | 530 |  |  |  |  |  |

| CCG | GAG | CAG | CAG | GAG | TTC | ATG | CAG | GCG | GTG | CGC | GAG | GTG | GCC | GTC | TCC | 192 |
|---|---|---|---|---|---|---|---|---|---|---|---|---|---|---|---|---|
| Pro | Glu | Gln | Gln | Glu | Phe | Met | Gln | Ala | Val | Arg | Glu | Val | Ala | Val | Ser |  |
| 535 |  |  |  |  | 540 |  |  |  |  | 545 |  |  |  |  | 550 |  |

| CTG | CAG | CCC | GTG | TTC | GAG | AAG | CGC | CCC | GAG | CTG | CTG | CCC | ATC | TTC | AAG | 240 |
|---|---|---|---|---|---|---|---|---|---|---|---|---|---|---|---|---|
| Leu | Gln | Pro | Val | Phe | Glu | Lys | Arg | Pro | Glu | Leu | Leu | Pro | Ile | Phe | Lys |  |
|  |  |  |  | 555 |  |  |  |  | 560 |  |  |  |  | 565 |  |  |

| CAG | ATC | GTT | GAG | CCT | GAG | CGC | GTG | ATC | ACC | TTC | CGC | GTG | TCC | TGG | CTG | 288 |
|---|---|---|---|---|---|---|---|---|---|---|---|---|---|---|---|---|
| Gln | Ile | Val | Glu | Pro | Glu | Arg | Val | Ile | Thr | Phe | Arg | Val | Ser | Trp | Leu |  |
|  |  |  | 570 |  |  |  |  | 575 |  |  |  |  | 580 |  |  |  |

| GAC | GAC | GCC | GGC | AAC | CTG | CAG | GTC | AAC | CGC | GGC | TTC | CGC | GTG | CAG | TAC | 336 |
|---|---|---|---|---|---|---|---|---|---|---|---|---|---|---|---|---|
| Asp | Asp | Ala | Gly | Asn | Leu | Gln | Val | Asn | Arg | Gly | Phe | Arg | Val | Gln | Tyr |  |
|  |  |  | 585 |  |  |  |  | 590 |  |  |  |  | 595 |  |  |  |

| | | | | | | | | | | | | | | | | |
|---|---|---|---|---|---|---|---|---|---|---|---|---|---|---|---|---|
| TCG | TCC | GCC | ATC | GGC | CCC | TAC | AAG | GGC | GGC | CTG | CGC | TTC | CAC | CCC | TCC | 384 |
| Ser | Ser | Ala | Ile | Gly | Pro | Tyr | Lys | Gly | Gly | Leu | Arg | Phe | His | Pro | Ser | |
| | | 600 | | | | 605 | | | | | 610 | | | | | |
| GTG | AAC | CTG | TCC | ATC | ATG | AAG | TTC | CTT | GCC | TTT | GAG | CAG | ATC | TTC | AAG | 432 |
| Val | Asn | Leu | Ser | Ile | Met | Lys | Phe | Leu | Ala | Phe | Glu | Gln | Ile | Phe | Lys | |
| 615 | | | | | 620 | | | | | 625 | | | | | 630 | |
| AAC | AGC | CTG | ACC | ACC | CTG | CCC | ATG | GGC | GGC | GGC | AAG | GGC | GGC | TCC | GAC | 480 |
| Asn | Ser | Leu | Thr | Thr | Leu | Pro | Met | Gly | Gly | Gly | Lys | Gly | Gly | Ser | Asp | |
| | | | | 635 | | | | | 640 | | | | | 645 | | |
| TTC | GAC | CCC | AAG | GGC | AAG | AGC | GAC | GCG | GAG | GTG | ATG | CGC | TTC | TGC | CAG | 528 |
| Phe | Asp | Pro | Lys | Gly | Lys | Ser | Asp | Ala | Glu | Val | Met | Arg | Phe | Cys | Gln | |
| | | | 650 | | | | | 655 | | | | | 660 | | | |
| TCC | TTC | ATG | ACC | GAG | CTG | CAG | CGC | CAC | ATC | AGC | TAC | GTG | CAG | GAC | GTG | 576 |
| Ser | Phe | Met | Thr | Glu | Leu | Gln | Arg | His | Ile | Ser | Tyr | Val | Gln | Asp | Val | |
| | | 665 | | | | | 670 | | | | | 675 | | | | |
| CCC | GCC | GGC | GAC | ATC | GGC | GTG | GGC | GCG | CGC | GAG | ATT | GGC | TAC | CTT | TTC | 624 |
| Pro | Ala | Gly | Asp | Ile | Gly | Val | Gly | Ala | Arg | Glu | Ile | Gly | Tyr | Leu | Phe | |
| | 680 | | | | | 685 | | | | | 690 | | | | | |
| GGC | CAG | TAC | AAG | CGC | ATC | ACC | AAG | AAC | TAC | ACC | GGC | GTG | CTG | ACC | CCG | 672 |
| Gly | Gln | Tyr | Lys | Arg | Ile | Thr | Lys | Asn | Tyr | Thr | Gly | Val | Leu | Thr | Pro | |
| 695 | | | | | 700 | | | | | 705 | | | | | 710 | |
| AAG | GGC | CAG | GAG | TAT | GGC | GGC | TCC | GAG | ATC | CGC | CCC | GAG | GCC | ACC | GGC | 720 |
| Lys | Gly | Gln | Glu | Tyr | Gly | Gly | Ser | Glu | Ile | Arg | Pro | Glu | Ala | Thr | Gly | |
| | | | | 715 | | | | | 720 | | | | | 725 | | |
| TAC | GGC | GCC | GTG | CTG | TTT | GTG | GAG | AAC | GTG | CTG | AAG | GAC | AAG | GGC | GAG | 768 |
| Tyr | Gly | Ala | Val | Leu | Phe | Val | Glu | Asn | Val | Leu | Lys | Asp | Lys | Gly | Glu | |
| | | | 730 | | | | | 735 | | | | | 740 | | | |
| AGC | CTC | AAG | GGC | AAG | CGC | TGC | CTG | GTG | TCT | GGC | GCG | GGC | AAC | GTG | GCC | 816 |
| Ser | Leu | Lys | Gly | Lys | Arg | Cys | Leu | Val | Ser | Gly | Ala | Gly | Asn | Val | Ala | |
| | | 745 | | | | | 750 | | | | | 755 | | | | |
| CAG | TAC | TGC | GCG | GAG | CTG | CTG | CTG | GAG | AAG | GGC | GCC | ATC | GTG | CTG | TCG | 864 |
| Gln | Tyr | Cys | Ala | Glu | Leu | Leu | Leu | Glu | Lys | Gly | Ala | Ile | Val | Leu | Ser | |
| | 760 | | | | | 765 | | | | | 770 | | | | | |
| CTG | TCC | GAC | TCC | CAG | GGC | TAC | GTG | TAC | GAG | CCC | AAC | GGC | TTC | ACG | CGC | 912 |
| Leu | Ser | Asp | Ser | Gln | Gly | Tyr | Val | Tyr | Glu | Pro | Asn | Gly | Phe | Thr | Arg | |
| 775 | | | | | 780 | | | | | 785 | | | | | 790 | |
| GAG | CAG | CTG | CAG | GCG | GTG | CAG | GAC | ATG | AAG | AAG | AAG | AAC | AAC | AGC | GCC | 960 |
| Glu | Gln | Leu | Gln | Ala | Val | Gln | Asp | Met | Lys | Lys | Lys | Asn | Asn | Ser | Ala | |
| | | | | 795 | | | | | 800 | | | | | 805 | | |
| CGC | ATC | TCC | GAG | TAC | AAG | AGC | GAC | ACC | GCC | GTG | TAT | GTG | GGC | GAC | CGC | 1008 |
| Arg | Ile | Ser | Glu | Tyr | Lys | Ser | Asp | Thr | Ala | Val | Tyr | Val | Gly | Asp | Arg | |
| | | | | 810 | | | | | 815 | | | | | 820 | | |
| CGC | AAG | CCT | TGG | GAG | CTG | GAC | TGC | CAG | GTG | GAC | ATC | GCC | TTC | CCC | TGC | 1056 |
| Arg | Lys | Pro | Trp | Glu | Leu | Asp | Cys | Gln | Val | Asp | Ile | Ala | Phe | Pro | Cys | |
| | | 825 | | | | | 830 | | | | | 835 | | | | |
| GCC | ACC | CAG | AAC | GAG | ATC | GAT | GAG | CAC | GAC | GCC | GAG | CTG | CTG | ATC | AAG | 1104 |
| Ala | Thr | Gln | Asn | Glu | Ile | Asp | Glu | His | Asp | Ala | Glu | Leu | Leu | Ile | Lys | |
| | 840 | | | | | 845 | | | | | 850 | | | | | |
| CAC | GGC | TGC | CAG | TAC | GTG | GTG | GAG | GGC | GCC | AAC | ATG | CCC | TCC | ACC | AAC | 1152 |
| His | Gly | Cys | Gln | Tyr | Val | Val | Glu | Gly | Ala | Asn | Met | Pro | Ser | Thr | Asn | |
| 855 | | | | | 860 | | | | | 865 | | | | | 870 | |
| GAG | GCC | ATC | CAC | AAG | TAC | AAC | AAG | GCC | GGC | ATC | ATC | TAC | TGC | CCC | GGC | 1200 |
| Glu | Ala | Ile | His | Lys | Tyr | Asn | Lys | Ala | Gly | Ile | Ile | Tyr | Cys | Pro | Gly | |
| | | | | 875 | | | | | 880 | | | | | 885 | | |
| AAG | GCG | GCC | AAC | GCC | GGC | GGC | GTG | GCG | GTC | AGC | GGC | CTG | GAG | ATG | ACC | 1248 |
| Lys | Ala | Ala | Asn | Ala | Gly | Gly | Val | Ala | Val | Ser | Gly | Leu | Glu | Met | Thr | |
| | | | 890 | | | | | 895 | | | | | 900 | | | |
| CAG | AAC | CGC | ATG | AGC | CTG | AAC | TGG | ACT | CGC | GAG | GAG | GTT | CGC | GAC | AAG | 1296 |
| Gln | Asn | Arg | Met | Ser | Leu | Asn | Trp | Thr | Arg | Glu | Glu | Val | Arg | Asp | Lys | |
| | | | | 905 | | | | | 910 | | | | | 915 | | |

| | | | | | | | | | | | | | | | | |
|---|---|---|---|---|---|---|---|---|---|---|---|---|---|---|---|---|
| CTG | GAG | CGC | ATC | ATG | AAG | GAC | ATC | TAC | GAC | TCC | GCC | ATG | GGG | CCG | TCC | 1344 |
| Leu | Glu | Arg | Ile | Met | Lys | Asp | Ile | Tyr | Asp | Ser | Ala | Met | Gly | Pro | Ser | |
| | 920 | | | | 925 | | | | | 930 | | | | | | |
| CGC | AGA | TAC | AAT | GTT | GAC | CTG | GCT | GCG | GGC | GCC | AAC | ATC | GCG | GGC | TTC | 1392 |
| Arg | Arg | Tyr | Asn | Val | Asp | Leu | Ala | Ala | Gly | Ala | Asn | Ile | Ala | Gly | Phe | |
| 935 | | | | | 940 | | | | | 945 | | | | | 950 | |
| ACC | AAG | GTG | GCT | GAT | GCC | GTC | AAG | GCC | CAG | GGC | GCT | GTT | TAAGCTGCCC | | | 1441 |
| Thr | Lys | Val | Ala | Asp | Ala | Val | Lys | Ala | Gln | Gly | Ala | Val | | | | |
| | | | | 955 | | | | | 960 | | | | | | | |

AGGCCCAAGC CACGGCTCAC CGGCAATCCA AC    1473

( 2 ) INFORMATION FOR SEQ ID NO:26:

( i ) SEQUENCE CHARACTERISTICS:
        ( A ) LENGTH: 476 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

| | | | | | | | | | | | | | | |
|---|---|---|---|---|---|---|---|---|---|---|---|---|---|---|
| Met | Asp | Ala | Thr | Thr | Gly | Asp | Phe | Thr | Ala | Leu | Gln | Lys | Ala | Val | Lys |
| 1 | | | | 5 | | | | | 10 | | | | | 15 | |
| Gln | Met | Ala | Thr | Lys | Ala | Gly | Thr | Glu | Gly | Leu | Val | His | Gly | Ile | Lys |
| | | | 20 | | | | 25 | | | | | 30 | | | |
| Asn | Pro | Asp | Val | Arg | Gln | Leu | Leu | Thr | Glu | Ile | Phe | Met | Lys | Asp | Pro |
| | | 35 | | | | 40 | | | | | 45 | | | | |
| Glu | Gln | Gln | Glu | Phe | Met | Gln | Ala | Val | Arg | Glu | Val | Ala | Val | Ser | Leu |
| | 50 | | | | 55 | | | | | 60 | | | | | |
| Gln | Pro | Val | Phe | Glu | Lys | Arg | Pro | Glu | Leu | Leu | Pro | Ile | Phe | Lys | Gln |
| 65 | | | | 70 | | | | | 75 | | | | | 80 | |
| Ile | Val | Glu | Pro | Glu | Arg | Val | Ile | Thr | Phe | Arg | Val | Ser | Trp | Leu | Asp |
| | | | 85 | | | | 90 | | | | | 95 | | | |
| Asp | Ala | Gly | Asn | Leu | Gln | Val | Asn | Arg | Gly | Phe | Arg | Val | Gln | Tyr | Ser |
| | | | 100 | | | | 105 | | | | | 110 | | | |
| Ser | Ala | Ile | Gly | Pro | Tyr | Lys | Gly | Gly | Leu | Arg | Phe | His | Pro | Ser | Val |
| | | 115 | | | | 120 | | | | | 125 | | | | |
| Asn | Leu | Ser | Ile | Met | Lys | Phe | Leu | Ala | Phe | Glu | Gln | Ile | Phe | Lys | Asn |
| | 130 | | | | 135 | | | | | 140 | | | | | |
| Ser | Leu | Thr | Thr | Leu | Pro | Met | Gly | Gly | Gly | Lys | Gly | Gly | Ser | Asp | Phe |
| 145 | | | | 150 | | | | | 155 | | | | | 160 | |
| Asp | Pro | Lys | Gly | Lys | Ser | Asp | Ala | Glu | Val | Met | Arg | Phe | Cys | Gln | Ser |
| | | | 165 | | | | 170 | | | | | 175 | | | |
| Phe | Met | Thr | Glu | Leu | Gln | Arg | His | Ile | Ser | Tyr | Val | Gln | Asp | Val | Pro |
| | | | 180 | | | | 185 | | | | | 190 | | | |
| Ala | Gly | Asp | Ile | Gly | Val | Gly | Ala | Arg | Glu | Ile | Gly | Tyr | Leu | Phe | Gly |
| | | 195 | | | | 200 | | | | | 205 | | | | |
| Gln | Tyr | Lys | Arg | Ile | Thr | Lys | Asn | Tyr | Thr | Gly | Val | Leu | Thr | Pro | Lys |
| | 210 | | | | 215 | | | | | 220 | | | | | |
| Gly | Gln | Glu | Tyr | Gly | Gly | Ser | Glu | Ile | Arg | Pro | Glu | Ala | Thr | Gly | Tyr |
| 225 | | | | 230 | | | | | 235 | | | | | 240 | |
| Gly | Ala | Val | Leu | Phe | Val | Glu | Asn | Val | Leu | Lys | Asp | Lys | Gly | Glu | Ser |
| | | | 245 | | | | 250 | | | | | 255 | | | |
| Leu | Lys | Gly | Lys | Arg | Cys | Leu | Val | Ser | Gly | Ala | Gly | Asn | Val | Ala | Gln |
| | | | 260 | | | | 265 | | | | | 270 | | | |
| Tyr | Cys | Ala | Glu | Leu | Leu | Leu | Glu | Lys | Gly | Ala | Ile | Val | Leu | Ser | Leu |
| | | 275 | | | | 280 | | | | | 285 | | | | |

| | | | | | | | | | | | | | |
|---|---|---|---|---|---|---|---|---|---|---|---|---|---|
| Ser | Asp 290 | Ser | Gln | Gly | Tyr | Val 295 | Tyr | Glu | Pro | Asn | Gly 300 | Phe | Thr | Arg | Glu |
| Gln 305 | Leu | Gln | Ala | Val | Gln 310 | Asp | Met | Lys | Lys | Lys 315 | Asn | Asn | Ser | Ala | Arg 320 |
| Ile | Ser | Glu | Tyr | Lys 325 | Ser | Asp | Thr | Ala | Val 330 | Tyr | Val | Gly | Asp | Arg 335 | Arg |
| Lys | Pro | Trp | Glu 340 | Leu | Asp | Cys | Gln | Val 345 | Asp | Ile | Ala | Phe | Pro 350 | Cys | Ala |
| Thr | Gln | Asn 355 | Glu | Ile | Asp | Glu | His 360 | Asp | Ala | Glu | Leu | Leu 365 | Ile | Lys | His |
| Gly | Cys 370 | Gln | Tyr | Val | Val | Glu 375 | Gly | Ala | Asn | Met | Pro 380 | Ser | Thr | Asn | Glu |
| Ala 385 | Ile | His | Lys | Tyr | Asn 390 | Lys | Ala | Gly | Ile | Ile 395 | Tyr | Cys | Pro | Gly | Lys 400 |
| Ala | Ala | Asn | Ala | Gly 405 | Gly | Val | Ala | Val | Ser 410 | Gly | Leu | Glu | Met | Thr 415 | Gln |
| Asn | Arg | Met | Ser 420 | Leu | Asn | Trp | Thr | Arg 425 | Glu | Glu | Val | Arg | Asp 430 | Lys | Leu |
| Glu | Arg | Ile 435 | Met | Lys | Asp | Ile | Tyr 440 | Asp | Ser | Ala | Met | Gly 445 | Pro | Ser | Arg |
| Arg | Tyr 450 | Asn | Val | Asp | Leu | Ala 455 | Ala | Gly | Ala | Asn | Ile 460 | Ala | Gly | Phe | Thr |
| Lys 465 | Val | Ala | Asp | Ala | Val 470 | Lys | Ala | Gln | Gly | Ala 475 | Val | | | | |

POLYPEPTIDES AND POLYNUCLEOTIDES RELATING TO THE α-AND β-SUBUNITS OF A GLUTAMATE DEHYDROGENASE AND METHODS OF USE

This invention was made with government support under USDA Competitive Grant Number 87-CRCR-1-2476. The government has certain rights in this invention.

BACKGROUND OF THE INVENTION

Inorganic nitrogen acquired by plants is ultimately converted to ammonium before being assimilated in organic nitrogen metabolism. One enzyme postulated to be involved in the assimilatory process is glutamate dehydrogenase (GDH), a group of ubiquitous enzymes found to be present in almost all organisms from microbes to higher plants and animals (Srivastava, H. S., R. P. Singh [1987] *Phytochem.* 26:597–610). GDH catalyses the reversible conversion of α-ketoglutarate to glutamate via a reductive amination that utilizes reduced β-nicotinamide adenine dinucleotide (NADH) or reduced β-nicotinamide adenine dinucleotide phosphate (NADPH) as a cofactor. The role of plant GDHs in the assimilation of ammonium into amino acids has been questioned since the discovery of the glutamine synthetase/glutamate synthase (GS/GOGAT) pathway that is believed to be the favored pathway for ammonium assimilation in higher plants (Miflin, B. J., P. J. Lea [1976] *Phytochem.* 15:873–885).

The primary objection to GDH playing a major role in plant nitrogen metabolism is its low affinity for ammonium that would require high intracellular ammonium concentrations to function anabolically. Early evidence indicated that GDH is a catabolic enzyme catalyzing the deamination of glutamate with only a partially anabolic function in synthesizing glutamate (Wallgrove, J. C., N. P. Hall; A. C. Kendall, [1987] *Plant Physiol.* 83:155–158). The physiological role of large amounts of GDH present in various plant tissues and organelles is still unclear, and possible conditions under which GDH may play a significant role in carbon and nitrogen metabolism have not been resolved.

The majority of plant GDHs characterized to date are localized in the mitochondria; however, a GDH species differing in several properties (i.e., cofactor specificity, $K_m$ values, organelle localization, thermal stability) has been characterized from the chloroplast of a unicellular green alga *Chlorella sorokiniana*. *C. sorokiniana* cells have been shown to possess a constitutive, mitochondrial, tetrameric NAD-specific GDH (Meredith, M. J., R. M. Gronostajski, R. R. Schmidt [1978] *Plant Physiol.* 61:967–974), and seven ammonium-inducible, chloroplast-localized, homo- and heterohexameric NADP-GDH isoenzymes (Prunkard, D. E., N. F. Bascomb, R. W. Robinson, R. R. Schmidt [1986] *Plant Physiol.* 81:349–355; Bascomb, N. F., R. R. Schmidt [1987] *Plant Physiol.* 83:75–84). The seven chloroplastic NADP-GDH isoenzymes were shown to have different electrophoretic mobilities during native-PAGE, and presumably result from the formation of homo- and heterohexamers composed of varying ratios of α- and β-subunits (53.5 and 52.3 kilodaltons, respectively).

Chlorella cells cultured in 1 to 2 mM ammonium medium accumulate only the α-homohexamer (Bascomb and Schmidt, supra). The addition of higher ammonium concentrations (3.4 to 29 mM) to nitrate-cultured cells results in the accumulation of both α- and β-subunits in NADP-GDH holoenzymes (Prunkard et al., supra; Bascomb and Schmidt, supra; Bascomb, N. F., D. E. Prunkard, R. R. Schmidt [1987] *Plant Physiol.* 83:85–91). Prunkard et al. (Prunkard, D. E., N. F. Bascomb, N. F, W. T. Molin, R. R. Schmidt [1986] *Plant Physiol.* 81:413–422) demonstrated that the NADP-GDH subunit ratio and isoenzyme pattern is influenced by both the carbon and nitrogen source as well as the light conditions under which cells are cultured.

α- and β-NADP-GDH homohexamers purified from Chlorella cells have strikingly different ammonium $K_m$ values; however, the $K_m$ values for their other substrates are very similar. The α-homohexamer (composed of six identical α-subunits) that catalyzes the biosynthesis of glutamate is allosterically regulated by NADPH and possesses an unusually low $K_m$ for ammonium that ranges from 0.02 to 3.5 mM, depending on the NADPH concentration (Bascomb and Schmidt, supra). The $K_m$ value for ammonium of the α-homohexamer is the lowest reported ammonium $K_m$ for any plant GDH characterized to date. In contrast, the β-homohexamer (catabolic form) is a non-allosteric enzyme with an ammonium $K_m$ of approximately 75 mM. From these studies involving purified enzymes, it is postulated that the heterohexamers have varying degrees of affinity for ammonium. However, no kinetic analyses have been performed on purified heterohexamers.

Although the α- and β-subunits have distinct in vivo turnover rates (Bascomb et al., supra) and the corresponding homohexamers have remarkably different ammonium $K_m$ values, the α- and β-subunits are derived from precursor proteins of nearly identical size (ca 58,000 Daltons) and were shown to have very similar peptide maps (Prunkard et al., supra; Bascomb and Schmidt, supra). Moreover, polyclonal antibodies prepared against the β-homohexamer are capable of immunoprecipitating all of the NADP-GDH isoenzymes (Yeung, A. T., K. J. Turner, N. F. Bascomb, R. R. Schmidt [1981]*Anal. Biochem.* 10:216–228; Bascomb et al., supra), but do not crossreact with the mitochondrial NAD-GDH. In addition, previous research in this laboratory provided genomic cloning and southern blot evidence that indicated the *C. sorokiniana* genome possesses a single NADP-GDH structural gene (Cock, J. M., K. D. Kim, P. W. Miller, R. G. Hutson, R. R. Schmidt [1991] *Plant Mol. Biol.* 17:17–27).

The *C. sorokiniana* nuclear-encoded chloroplastic NADP-specific glutamate dehydrogenases are the only chloroplastic localized GDH sequences isolated and characterized from plants. Although the Chlorella GDH isoenzymes had been well characterized, it has been discovered in the present invention that the two mature subunits arise via specific processing of two similar precursor proteins encoded by two mRNAs formed by alternative splicing of a pre-mRNA derived from a single nuclear gene. Furthermore, the identification of the cleavage site and amino-terminal peptide sequence of the mature functional GDH subunits critical to understanding the enzymatic regulation previously demonstrated in vitro had not been accomplished prior to the present invention.

BRIEF SUMMARY OF THE INVENTION

The present invention provides the isolation and characterization of two full-length cDNAs from mRNAs isolated from the unicellular green algae *Chlorella sorokiniana*. The two cDNAs encode the precursor proteins (56.35 kD; 57.85 kD) that are processed to yield the mature α- and β-subunits (53.5 kD; 52.3 kD, respectively) that compose the active NADP-GDH hexameric isoenzymes. The present invention demonstrates that the single NADP-GDH gene is alternatively spliced to yield two mRNAs that encode two different chloroplast precursor proteins which are processed to the mature α- and β-subunits. Also described are useful fragments or mutants of the nucleotide and amino acid sequences which retain the disclosed activity or utility. For example, certain fragments of the amino acid sequences provided herein can be useful as transit peptides, providing the protein with the capability to enter and remain in certain cell compartments. Fragments of the nucleotide sequences which are described herein can be useful, for example, as primers in amplification procedures or as probes to hybridize to complementary sequences of interest. The nucleotide and amino acid sequences and fragments thereof as described herein can also be useful as molecular weight markers or in identifying and conforming the relatedness of other nucleotide sequences, polypeptides, or isoenzymes which pertain to NADP-GDH.

The present invention provides a method to alter the assimilation of inorganic nitrogen into organic nitrogen metabolism of higher plants by expressing glutamate dehydrogenases from *C. sorokiniana* and/or GDHs isolated from other organisms. The alteration of nitrogen assimilation can have the effect of increasing nitrogen assimilation which, as is well understood in the art, can affect the composition of the plant through the inverse effect on carbon metabolism, e.g., accumulation of carbohydrates. It further provides DNA constructs for use in these methods. The present invention also provides the identification of the amino-terminal sequences of the α- and β-subunits, thus providing the precise molecular information needed to express the GDH with the unique kinetic properties of the *C. sorokiniana* chloroplastic α- and β-NADP-GDH homohexamers. The present invention also provides crops having an increased yield, improved ammonia assimilatory properties which increase their tolerance of ammonia toxicity, improved osmotic stress tolerance, and improved composition of the crop.

BRIEF DESCRIPTION OF THE SEQUENCES

SEQ ID NO: 1 is the cDNA for the precursor-protein of the α-subunit of an NADP-specific glutamate dehydrogenase.

SEQ ID NO: 2 is the deduced amino acid sequence of the polynucleotide of SEQ ID NO. 1.

SEQ ID NO: 3 is the cDNA for the precursor-protein of the β-subunit of an NADP-specific glutamate dehydrogenase.

SEQ ID NO: 4 is the deduced amino acid sequence of the polynucleotide of SEQ ID NO. 3.

SEQ ID NO: 5 is the N-terminal sequence for the NADP-GDH α-subunit.

SEQ ID NO: 6 is the N-terminal sequence for the NADP-GDH β-subunit.

SEQ ID NO: 7 is the cDNA sequence in the clone designated pBGDc53.

SEQ ID NO: 8 is a primer which hybridizes to the conserved region of NADP-GDH mRNAs.

SEQ ID NO: 9 is a poly(dT) polynucleotide used as an adaptor primer according to the subject invention.

SEQ ID NO: 10 is a polynucleotide used as a primer according to the subject invention.

SEQ ID NO: 11 is a polynucleotide used as a primer according to the subject invention.

SEQ ID NO: 12 is a polynucleotide used as an adaptor primer according to the subject invention.

SEQ ID NO: 13 is the polynucleotide insert in the clone designated pRGDc 60.

SEQ ID NO: 14 is the polynucleotide insert in the clone designated pRGDc 61.

SEQ ID NO: 15 is the polynucleotide used as a primer according to the subject invention.

SEQ ID NO: 16 is the polynucleotide insert in a clone designated pGDc 63.

SEQ ID NO: 17 is the polynucleotide insert of a clone designated pGDc 64.

SEQ ID NO: 18 is the polynucleotide resulting from ligation of purified fragments of the inserts in the clones designated pBGDc 53 and pGDc 63, according to the subject invention.

SEQ ID NO: 19 is the polynucleotide resulting from ligation of purified inserts of the clones designated pGDc 64 and pBGDc 53.

SEQ ID NO: 20 is a polynucleotide used as a primer according to the subject invention.

SEQ ID NO: 21 is a polynucleotide used as a primer hybridizing to the 3' terminus of the template DNA according to the subject invention.

SEQ ID NO: 22 is a polynucleotide used as a primer according to the subject invention.

SEQ ID NO: 23 is the polynucleotide sequence (cDNA) of the processed, mature NADP-GDH α-subunit.

SEQ ID NO: 24 is the amino acid sequence of the processed, mature NADP-GDH α-subunit.

SEQ ID NO: 25 is the polynucleotide (cDNA) sequence of the processed, mature NADP-GDH β-subunit.

SEQ ID NO: 26 is the amino acid sequence of the processed, mature NADP-GDH β-subunit.

DETAILED DISCLOSURE OF THE INVENTION

The present invention provides, for example, cDNAs for the precursor-proteins of the α- and β-subunits of the ammonium inducible, chloroplast localized NADP-specific glutamate dehydrogenases from *Chlorella sorokiniana* as shown in SEQ ID NOS: 1 and 3, respectively. The deduced amino acid sequences for the precursor-proteins of the α- and β-subunits of the ammonium inducible, chloroplast localized NADP-specific glutamate dehydrogenases from *Chlorella sorokiniana* are shown in SEQ ID NOS: 2 and 4, respectively.

*E. coli* hosts containing cDNA inserts were deposited with the American Type Culture Collection (ATCC), 12301 Parklawn Drive, Rockville, Md. 20852 USA. The cultures were assigned the following accession numbers by the repository:

| Culture | Accession number | Deposit date |
| --- | --- | --- |
| *E. coli* DH5α α-NADP-GDH SEQ No. 1 (+42 bp) | ATCC 69925 | October 6, 1995 |
| *E. coli* DH5α β-NADP-GDH SEQ No. 1 (−42 bp) | ATCC 69926 | October 6, 1995 |

The subject cultures have been deposited under conditions that assure that access to the culture(s) will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit(s), and in any case, for a period of at least 30 (thirty) years after the date of deposit or for the enforceable life of any patent which may issue disclosing the cultures. The depositor acknowledges the duty to replace the deposit (s) should the depository be unable to furnish a sample when requested, due to the condition of the deposit(s). All restrictions on the availability to the public of the subject culture deposits will be irrevocably removed upon the granting of a patent disclosing them.

Automated amino acid sequence analysis identifies 20 and 10 amino-terminal amino acid residues of the α- and β-subunits, respectively. Alignment of the α- and β-subunit peptide sequences reveals that the two subunits are identical with the exception of an 11-amino acid extension present in the larger α-subunit. Monoclonal antibodies raised against the α-subunit were shown to recognize the β-subunit providing further evidence that the two subunits are nearly identical. The identification of the unique α- and β-subunit processing sites within the precursor proteins provides the molecular mechanism to explain the different kinetic properties of the α- and β-NADP-GDH homohexameric isoenzymes.

The aforementioned data provide the information necessary to engineer plants with a specific GDH that has favorable kinetic properties to influence both carbon and nitrogen metabolism. Based on the high guanine/cytosine content the cDNAs are highly amenable for heterologous expression in higher plants. The introduction of either or both subunits with their chloroplast targeting sequences or with other organellar targeting sequences in heterologous plant systems can improve nitrogen assimilation and influence the carbon/nitrogen balance.

It has been discovered that chloroplast localization is related to, and can be dependent on, the N-terminus of the α- or β-precursor protein. Cleavage of the N-terminus of the precursors yields the mature protein. Accordingly, the chloroplast transit peptide comprises a peptide which forms or is an active fragment which is part of the N-terminus cleaved from the precursor protein. Peptides having conformation similar to these cleaved peptides can also function as transit peptides. The chloroplast-transit peptide comprises the active fragment of the N-terminal peptide cleaved from the α-precursor (a 40-mer) or the β-precursor (a 37-mer). The polynucleotide sequences encoding the chloroplast-transit peptides can be used by persons of ordinary skill in the art to produce chloroplast-transit peptides employed with the peptides described herein, or others known in the art.

Adding, removing, or replacing the chloroplast transit peptide associated with the GDH enzyme can be employed to localize the protein according to need, by means well known in the art. For example, localization of the enzyme in a chloroplast of a cell can be achieved by the insertion of a chloroplast transit peptide onto an amino acid sequence lacking such a transit peptide. Species-specific chloroplast-transit peptides can be added or can replace those present to optimize insertion into the chloroplast of a desired species. Similarly, removal of a chloroplast-transit peptide or production of a recombinant protein lacking the peptide can be utilized to sequester the protein in a cellular compartment other than the chloroplast.

Transformed plants expressing the α-homohexamer can be more tolerant to ammonia toxicity, assimilate ammonium more efficiently, and respond more rapidly to osmotic stress encountered in transiently saline soils by providing glutamate the precursor to the osmoprotectant proline. Expression of, for example, the β-homohexamer or GDH heterohexamers can be used to alter the rate of nitrogen assimilation, favoring accumulation of carbohydrates in fruits and other storage organs.

Following are examples which illustrate procedures, including the best mode, for practicing the invention. These examples should not be construed as limiting. All percentages are by weight and all solvent mixture proportions are by volume unless otherwise noted.

EXAMPLES

*C. sorokiniana* chloroplast glutamate dehydrogenases. The chloroplastic glutamate dehydrogenase α- and β-isoenzymes used in the following experiments are naturally produced by an organism characterized as *Chlorella sorokiniana*.

For kinetic characterization in both the aminating and deaminating directions, the α- and β-holoenzymes were purified from cells that were accumulating only one form of homohexameric GDH isoenzyme. Table 1 summarizes the $K_m$ values determined for both the α- and β-homohexameric isoenzyme aminating reaction.

TABLE 1

| GDH Isoform | Substrate | $K_m$ Value (mM) |
|---|---|---|
| α-homohexamer | NADPH | 0.14 |
| | $NH_4^+$ | 0.02–3.5 |
| | α-ketoglutarate | 0.35* |
| β-homohexamer | NADPH | 0.14 |
| | $NH_4^+$ | 77 |
| | α-ketoglutarate | 12 |

*after Shatilov, V. R., W. L. Kretovich (1977) Mol. Cell Biochem. 15:201–212.

Table 2 summarizes the $K_m$ values determine for both the α- and β-homohexameric isoenzyme deaminating reaction.

TABLE 2

| GDH Isoform | Substrate | $K_m$ Value (mM) |
|---|---|---|
| α-homohexamer | $NADP^+$ | 0.04 |
| | Glutamate | 38.2 |
| β-homohexamer | NADP+ | 0.04 |
| | Glutamate | 32.3 |

*C. sorokiniana* culture conditions. The *C. sorokiniana* cells (UTEX-1230, University of Texas algal culture collection; 3B2NA, Robert R. Schmidt, University of Florida, Microbiology Cell Science Department) were cultured autotrophically as previously described by Prunkard et al., supra in a modified basal salts medium. The modified medium contained in mM concentration: $CaCl_2$, 0.34; $K_2SO_4$, 6.0; $KH_2PO_4$, 18.4; $MgCl_2$, 1.5; in μM concentration $CoCl_2$, 0.189; $CuCl_2$, 0.352; EDTA, 72; $FeCl_3$, 71.6; $H_3BO_3$, 38.8; $MnCl_2$, 10.1; $NH_4VO_4$, 0.20; $(NH_4)_6MO_7O_{24}$, 4.19; $NiCl_2$, 0.19; $SnCl_2$, 0.19; $ZnCl_2$, 0.734. The medium was supplemented with 1 mM $NH_4Cl$, 29 mM $NH_4Cl$, or 29 mM $KNO_3$ as a nitrogen source depending on the experimental conditions. The medium containing $NH_4Cl$ was adjusted to pH 7.4, and medium containing $KNO_3$ was adjusted to pH 6.8 with KOH after autoclaving. Cells were supplied with a 2% (v/v) $CO_2$-air mixture and light intensity sufficient to allow cell division into four progeny.

Purification of the NADP-GDH isoenzymes. For purification of the glutamate dehydrogenase α-isoenzyme, *C.*

*sorokiniana* cells were cultured with continuous light in 29 mM ammonium medium in a 30 L Plexiglas chamber as previously described (Baker, A. L., R. R. Schmidt [1963] *Biochim. Biophys. Acta* 74:75–83). Cells were harvested at 4.0 OD$_{640}$ by centrifugation at 30,000 rpm through a Sharples centrifuge and washed two times in 10 mM Tris (pH 8.5 at 4° C.). Pelleted cells (130 g) were stored at −20° C. in 250 mL centrifuge bottles until use. Purification of NADP-GDH was accomplished using a modified procedure of Yeung et al., supra. Procedural modifications involved the substitution of Sephadex G-200 gel (Pharmacia) for G-150 gel in the gel-filtration column, and the addition of NADP$^+$ as a stabilizer to a final concentration of 0.1 mM to the gel-filtration buffer and all subsequent storage buffers. As a final modification, the NADP$^+$ affinity resin step was omitted and a preparative nondenaturing-PAGE step was substituted (Miller, P. W., W. D. Dunn, R. R. Schmidt [1994] *BioRad US/EG Bulletin* 1897).

The GDH deaminating enzyme assay solution was composed of 44 mM Tris, 20.4 mM glutamate, and 1.02 mM NADP$^+$, pH 8.8. The aminating assay solution was composed of 50 mM Tris, 25 mM α-ketoglutarate, 0.357 mM NADPH, and 0.356M (NH$_4$)$_2$SO$_4$, pH 7.4. One unit of enzyme activity was the amount of NADP-GDH required to reduce or to oxidize 1.0 μmol of NADP$^+$ or NADPH per minute at 38.5° C.

Sephadex G-200 column fractions possessing NADP-GDH activity were pooled and concentrated via Diaflow filtration. The soluble enzyme (68 mg) was protected from oxidation by the addition of DTT to a final concentration of 10 mM, and dialyzed for 30 minutes against 28.8 mM Tris, 192 mM glycine, 2 mM DTT (pH 8.4). The dialysate was clarified by centrifugation at 20,000 g for 10 minutes at 4° C. and was combined with 3 mL of 40% (w/v) sucrose and 1 mL of 0.02% bromophenol blue.

For preparative nondenaturing PAGE, a 3 cm tall 7% acrylamide (w/v, 28 acrylamide: 0.735 bis-acrylamide, pH 8.8) resolving gel, and a 2 cm tall 2% acrylamide (w/v, 1.6 acrylamide: 0.4 bis-acrylamide, pH 6.6) stacking gel were cast in the 28 mm ID gel tube of the Model 491 Prep Cell. All acrylamide stocks were pretreated with AG501-X8 mixed bed resin to remove any contaminating acrylic acid residue to prevent in vitro N-acylation of proteins during electrophoresis. The protein sample was electrophoresed at 15 mA constant power for 20 minutes and then for 3.5 hours at a constant power of 30 mA. Six milliliter fractions were collected and assayed for NADP-GDH deaminating activity and GDH containing fractions were pooled. The enzyme in the pooled fractions in 10 mM KPO$_4$ (pH 6.2), 0.1 mM NADP$^+$ was concentrated by Diaflow ultrafiltration to 1 mg/mL as determined by the method of Bradford, using BSA as a standard. The concentrated enzyme preparation was stored at −20° C. The purity of the preparation was determined by silver-staining to visualize proteins resolved by 10% (w/v) Tris-Tricine SDS-PAGE (Schagger, H., G. von Jagow [1987] *Anal. Biochem.* 166:368–379).

The NADP-GDH β-isoenzyme was purified from a mixture of cells cultured for 240 minutes in 1 mM ammonium medium (14 g), 90 minutes in 1 mM ammonium medium (6 g), and for 20, 40, 60, and 80 minutes in 29 mM ammonium medium (1 g/time point) according to Bascomb and Schmidt, supra. The NADP-GDH β-isoenzyme was partially purified using a scaled down modified procedure of Yeung et al., supra. The DEAE sephacel ion exchange columns (pH 7.4, and pH 6) were scaled down to a 40 mL bed volume and a 400 mL linear KCl gradient (0 to 0.4M) was used to elute the proteins in 3 mL fractions. The pH 6 DEAE ion-exchange column fractions containing NADP-GDH were combined into two pools; corresponding to the leading and trailing halves of the NADP-GDH activity peak. The separate pooled fractions were dialyzed against 10 mM KPO$_4$ (pH 6.2), 2 mM DTT for 16 hours, and affinity purified using Type 3 NADP$^+$ affinity gel (Pharmacia) as previously described (Bascomb and Schmidt, supra). The NADP-GDH in the pooled fractions was concentrated via Diaflow ultrafiltration to 2 mg/ml protein, as determined by the method of Bradford (Bradford, M. M. [1976] *Anal. Biochem.* 72:248–254), and stored at 4° C. until further use. After resolution of the proteins by 8% (w/v) Tris-Tricine SDS-PAGE, the purity of the preparation was determined by silver staining.

Amino-terminal sequencing of the mature subunits. An aliquot of a preparation of purified NADP-GDH α-subunit (120 pmol) and a partially purified preparation of NADP-GDH α-subunit (80 pmol) and β-subunit (50 pmol) were resolved by 8% (w/v) Tris-Tricine SDS-PAGE and electroblotted to a PVDF membrane (Immobilon-P$^{SQ}$, Millipore) as described by Plough et al. (Plough, M., A. L. Jensen, V. Barkholt [1989] *Anal. Biochem.* 181:33–39). To prevent in vitro acylation of the protein amino-terminal residues, all polyacrylamide solutions used in PAGE were treated with AG501-X8 mixed bed resin to remove contaminating acrylic acid. An Applied Biosystems, Inc. model 470A gas phase sequencer was utilized for automated Edman degradation amino sequence analysis. The PTH-aa derivatives were identified by RP-HPLC. Protein sequence analysis of the electroblotted proteins was provided by the Interdisciplinary Center for Biotechnology Research Protein Chemistry Core facility at the University of Florida.

The following N-terminal sequence was determined for the α-subunit: AVSLEEQISAMDATTGDFTA (SEQ ID NO: 5). The following N-terminal sequence was determined for the β-subunit: DATTGDFTAL (SEQ ID NO: 6). These sequences are identical to the ORF identified in the two NADP-GDH cDNAs and indicate the positions of the internal cleavage sites utilized to remove the chloroplast targeting peptide sequences. The chloroplast targeting peptide sequences (or chloroplast-transit peptides) can be useful for cell compartment localization with these and other amino acid sequences. The polynucleotides encoding the chloroplast-transit peptides can be used with other polynucleotide sequences to encode chloroplast-transit peptides.

cDNA isolation and sequencing. A pellet of *C. sorokiniana* cells stored at −70° C. was resuspended 1 to 10 (w/v) in RNA breakage buffer: 0.1M Tris (pH8.5), 0.4M LiCl, 10 mM EGTA, 5 mM EDTA, 100 units/mL sodium heparin (Sigma, 100 units/mg), and 1 mM aurintricarboxylic acid (Sigma). The cell suspension was centrifuged at 7000 g for 5 minutes at 4° C. and the supernatant was discarded. The cell pellet was resuspended 1 to 10 (w/v) in RNA breakage buffer and ruptured by passage through a French pressure cell at 20,000 p.s.i. The cell homogenate was collected in a disposable 50 mL conical tube containing 0.05 times volume 20% (w/v) SDS, 0.05 times volume 0.5M EDTA (pH 8), 200 μg/mL proteinase K, and allowed to incubate at room temperature for 15 minutes. One-half volume of TE buffer (Tris 10 mM:EDTA 1mM, pH 8.0) equilibrated phenol was added to the homogenate and after a 3 minutes incubation a one-half volume of chloroform:isoamylalcohol (24:1, v/v) was added and mixed for 10 minutes on a wrist action shaker. The extracted homogenate was transferred to a 30 mL siliconized corex tube and centrifuged at 1000 g for 10 minutes at 4° C. The upper aqueous phase was removed and repeatedly extracted with an equal volume of chloroform:isoamyl-alcohol (24:1, v/v), as described above, until the aqueous interface was clear. After the final extraction, the aqueous phase was combined with an equal volume of 2× LiCl-Urea buffer (4M LiCl, 4M urea, 2 mM EDTA, 1 mM aurintricarboxylic acid; Sigma) and the RNA was precipitated on ice for 16 hours at 4° C. The RNA precipitate was centrifuged at 4000 g for 20 minutes at 4° C. and the resulting pellet was rinsed once with 1× LiCl-Urea buffer and centrifuged again to pellet the RNA. The RNA pellet was solubilized in TE (pH 7.5) and an aliquot was quantified spectrophotometrically at 260 nm. After quantitation, the mRNA fraction was isolated from total cellular RNA using an oligo(dT) spin column kit. Poly(A)$^+$ RNA (50 μg) from each preparation was combined and utilized for the commercial production of a custom λUni-ZAP XR *C. sorokiniana* cDNA library (Stratagene Cloning Systems, Palo Alto, Calif.).

The amplified λZAP library, containing 2×10$^{10}$ pfu/mL, was plated on twenty 150 mm petri plates at 50,000 pfu per plate for a total of 1×10$^6$ pfu screened. The phage plaques were absorbed to duplicate Hybond-N 132 mm circular membranes and treated according to the plaque blotting protocol of Amersham (1985, Amersham International plc, Arlington Heights, Ill.). Membranes were prehybridized in a common container in 200 mL of 2× PIPES (0.8M NaCl, 20 mM PIPES, pH 6.5), 50% (w/v) formamide, 0.5% (w/v) SDS, 100μg/mL denatured sheared salmon sperm DNA at 40° C. Blocked membranes were hybridized at 42° C. in ten heat-sealable bags (four membranes/bag) in prehybridization buffer containing 1×10$^6$ cpm/membrane of a $^{32}$P-labeled NADP-GDH 242 bp HCR cDNA probe on a lab rocker. The membranes were washed three times in 200 mL of 0.1× SSC, 0.1% (w/v) SDS for 20 minutes per wash at 50° C. Duplicate membranes were wrapped in plastic wrap and exposed to Kodak X-Omat AR film at −70° C. for 28 hours. Putative NADP-GDH cDNA plaques, detected on duplicate membranes, were cored from the plate and plaque purified by secondary and tertiary screenings with the 242 bp conserved region probe. Putative NADP-GDH cDNA phage clones, selected in the primary screening, were combined and screened a second time with a $^{32}$P-labeled 130 bp Eco RI/Bgl II cDNA fragment isolated from the 5' terminus of the most complete 5' end NADP-GDH cDNA clone. Ten plaque pure NADP-GDH clones were subcloned in pBluescript KS$^+$ (Stratagene) and transformed into *E. coli* DH5α F' (Bethesda Research Laboratories, BRL) via an in vivo excision protocol provided by Stratagene. All plasmid isolations were performed as described by Kraft et al. (Kraft, R., J. Tardiff, K. S. Krauter, L. A. Leinwand [1988] *Biotechniques* 6:544–547). Sequence analysis revealed all ten clones were identical at their 3'-termini and differed by varying degrees of truncation at their 5'-termini. The longest cDNA clone with a complete 3'-terminus designated pBGDc53 (SEQ ID NO: 7) was not long enough to encode either subunit; therefore, the 5'-terminal sequences were determined by RACE PCR.

The 5'-terminal NADP-GDH cDNA sequences were cloned using a modified anchored PCR procedure for the rapid amplification of cDNA ends (Frohman, M. A. [1990] In D. H. Gelford, J. J. Snincky, T. J. White, eds, *PCR Protocols*, Academic Press, San Diego, Calif., pp 28–38; Jain, R., R. H. Gorner, J. J. Murtagh [1992] *Biotechniques* 12:58–59). A mixture of poly(A)$^+$ RNA, used in the synthesis of the λZAP library, was utilized to clone the 5' end of the NADP-GDH mRNA. One hundred nanograms of the mRNA mixture were combined with 10 ng of a gene-specific primer (5'-CTCAAAGGCAAGGAACTTCATG-3', SEQ ID NO: 8), designed to hybridize to the conserved region of NADP-GDH mRNAs, heated for 5 minutes, and chilled on ice. First strand DNA synthesis was performed using Superscript™ reverse transcriptase (BRL) according to the supplier's protocol. The terminated reverse transcription reaction was treated with one unit of ribonuclease H for 20 minutes at 37° C., 5 minutes at 95° C., and extracted once with chloroform:isoamyl alcohol (24:1, v/v). Excess primers and dNTPs were removed by centrifugation at 2000 rpm through an Ultrafree-MC filterfuge tube (30,000 MW cutoff, Millipore) and the retentate was concentrated to 10 μl on a Savant Speedvac. The first-strand synthesis products were combined with 10 μL of tailing mix (1× tailing buffer [Promega Corp.], 0.4 mM dATP, 10 units terminal deoxytransferase) and incubated at 37° C. for 10 minutes. The reaction mixture was heated to 95° C. for 5 minutes, diluted to 0.5 mL with TE (pH 8), and utilized as a cDNA pool. A mixture of 5 μL of the cDNA pool, 5 μL of Vent™ polymerase 10× buffer (New England Biolabs), 200 μM of each dNTP, 25 pmol of a gene specific primer (SEQ ID NO: 8), 5 pmol of the poly(dT) adaptor primer (5'-GGGTCGACATTCTAGACAGAATTCGTGGATCC(T)$_{18}$-3'; SEQ ID NO: 9), 0.2 units Perfectmatch™ DNA polymerase enhancer (Stratagene), and 1 unit of Vent™ polymerase (NEB) in 50 μL was amplified according to Jain et al., supra. The PCR products were purified away from the excess primers by centrifugation at 2,000 rpm through an Ultrafree-MC unit. The retentate was collected and subjected to two more rounds of amplification using a new nested gene specific primer at each step (5'-GGACGAGTACTGCACGC-3', SEQ ID NO: 10; 5'-GATCTCGGTCAGCAGCTG-3', SEQ ID NO: 11, respectively) and an adaptor primer (5'-GGGTCGACATTCTAGACAGAA-3'; SEQ ID NO: 12). PCR amplifications were performed in a Model 480 thermocycler (Perkin-Elmer Cetus), and all custom oligonucleotides were synthesized by the ICBR DNA synthesis facility, University of Florida. The standard PCR reaction mixture consisted of 10 μL of 10× Vent™ polymerase buffer, 100 μM of each dNTP, 0.4 units of Perfectmatch™, 50 pmol of each primer, 1 unit Vent™ DNA polymerase in a 100 μl reaction volume. The 5' RACE-PCR products were gel purified, subcloned into the SmaI site of pUC 18, and transformed into *E. coli* DH5α for further characterization. RACE PCR identified two 5' cDNA clones, which overlapped with the previously identified pBGDc 53 clone, that differed by a 42 nt insert identified in one clone designated pRGDc 60 (SEQ ID NO: 13) and lacking in the second cDNA designated pRGDc 61 (SEQ ID NO: 14).

Two additional cDNA clones lacking the RACE PCR polylinker, but possessing the complete 5'-termini corresponding to pRGDc 60 and 61 were constructed by RT-PCR amplification from mRNA using reaction conditions as described above and the gene specific primer pair (5'-CITICTGCTCGCCCTCTC-3', SEQ ID NO: 15, and SEQ ID NO: 11, above). The two PCR products were cloned into the SmaI site of pBluescript SK+ (Stratagene) and transformed into *E. coli* DH5α for further characterization. The cDNA clone that possessed the 42 nt insert was designated pGDc 63 (SEQ ID NO: 16) whereas the cDNA lacking the insert was designated pGDc 64 (SEQ ID NO: 17).

Full-length NADP-GDH cDNAs were constructed by restriction endonuclease treating pGDc 63 and 64 with EcoRI/ApaLI and gel purifying the resultant (264 bp; 222 bp, respectively) fragments. The gel purified fragments were ligated to a purified ApaLI/XhoI restriction fragment of pBGDc 53 and the full length ligation products (SEQ ID NO: 18; SEQ ID NO: 19) were gel agarose gel purified and utilized in subsequent PCR reactions.

Expression of α- and β-homohexamers in E. coli. Using the gel purified product (SEQ ID NO. 18), PCR mutagenesis was performed to remove the chloroplast targeting signal from the full-length cDNA and yield cDNAs encoding specifically the mature α- and β-subunits. Two sets of primer pairs were designed to synthesize α- and β-GDH subunit genes.

The following primer was designed to add a methionine to the amino terminus of the processed mature α-NADP-GDH subunit (alanine-41) to allow translation initiation and to generate a 5' NdeI site for subcloning purposes: 5'-CATATGGCCGTCTCGCTGGAGGAG-3' (SEQ ID NO: 20). The following second primer was designed to hybridize to the 3' terminus of the template DNA at a position 20 nt 3' of the endogenous TAA termination codon: 5'-GTTGGATTGCCGGTGAGCC-3' (SEQ ID NO: 21).

The following primer was designed to add a methionine to the amino terminus of the processed mature β-subunit (aspartate-38) to allow translation initiation and to generate a 5' NdeI site for subcloning purposes: 5'-CATATGGACGCCACCACCGGC-3' (SEQ ID NO: 22). The second 3' primer used in the PCR amplification was the 3'-terminus primer (SEQ ID NO: 21) described for the α-subunit amplification.

PCR cycling conditions were as follows: 95° C., 50 seconds; 64° C., 1 minute; 72° C., 1 minute 35 seconds (30 cycles). Primer, dNTP, Vent polymerase, and other reaction component concentrations were as previously described. The 1506 bp α-NADP-GDH subunit gene (SEQ ID NO: 23) and 1473 bp β-GDH subunit gene (SEQ ID NO: 25) PCR products were gel purified and given a 3' adenine nucleotide overhang by incubating the purified fragment with 100 μM dATP and Taq polymerase for 15 minutes at 72° C. The modified PCR products were cloned into the PCRII T/A cloning vector (Invitrogen) and transformed into competent E. coli cells. Clones bearing the inserts were selected by blue-white screening, plasmid purified, and digested with NdeIlBamHI to select for the proper orientation in the cloning vector. The selected plasmids were restricted with NdeI and BamHI (BamHI site provided by vector) and directionally cloned under the control of the IPTG inducible T7 polymerase promoter of pET 11a and pET 15b bacterial expression vectors (Novagen) linearized with NdeI/BamHI, and transformed into DH5α. Transformants were screened by NdeI/BamHI restriction analysis and clones possessing the properly oriented α- and β-subunit cDNAs (SEQ ID NO: 23; SEQ ID NO: 25) were selected, plasmid purified, and transformed into E. coli BL21(DE3) for protein expression purposes.

E. coli BL21(DE3) cells transformed with pET 11a-α-cDNA and pET 11a-β-cDNA constructs were induced with 100 mM IPTG for 1 hour. Protein extracts from the induced cells were tested by enzyme analysis for NADP-GDH activity, and the denatured proteins were resolved by SDS gel electrophoresis, and visualized by coomassie staining. The proteins expressed by the mature α-subunit cDNA (SEQ ID NO: 23) and the β-subunit cDNA (SEQ ID NO: 25) have the amino acid sequences shown in SEQ ID NO: 24 (α-subunit) and SEQ ID NO: 26 (β-subunit). The recombinant GDH subunits were verified by crossreactivity with rabbit anti-Chlorella NADP-GDH antibodies.

Under conditions not optimized for maximal induction, the E. coli cells, possessing the α- and β-GDH cDNAs and induced with IPTG, showed 60- and 7,000-fold increases in NADP-GDH activity relative to uninduced controls, respectively. The recombinant α- and β-NADP-GDHs are currently being analyzed to verify kinetic and biochemical properties.

The over-expression and assembly of the C. sorokiniana chloroplastic GDHs into active enzymes provides proof that the DNA constructs engineered via PCR are transcribed and translated into authentic proteins. The aforementioned constructs were then utilized for cytosolic expression of the algal GDHs in transgenic plants.

Transformation of plants. A method for producing genetically transformed plants that express increased levels of a specific GDH requires the introduction of a double-stranded recombinant DNA molecule into the nuclear genome of a plant cell. The DNA molecule must (1) contain a structural DNA for the GDH enzyme being introduced into the plant cell; (2) possess a promoter which functions in plants to regulate the production of an RNA sequence in a constitutive or tissue-specific manner by RNA polymerase enzyme; and (3) have a 3'-untranslated region which functions to cause transcriptional termination and the addition of polyadenylated nucleotides to the 3' end of the RNA. The resulting primary RNA molecule is subsequently processed in the nucleus, a process which involves the removal of intronic sequences and the addition of polyadenylate nucleotides to the 3' end of the mRNA.

Promoters which are useful in the present invention are those that can initiate transcription in a constitutive manner or in a tissue-specific manner where glutamate production or catabolism is desired. An example of a useful constitutive promoter is the CaMV enhanced 35S promoter that directs the synthesis of RNA in a tissue independent manner. Promoters which cause production of GDH specifically in seeds, stems, roots, leaves, or specific cell types in these tissues are useful in the present invention. For example, the seed-specific Phaseolin promoter is one such tissue-specific promoter. Thus native promoters for maize, wheat, barley, and rice may be obtained and used in the present invention as well as heterologous promoters from other organisms shown to function in a constitutive/tissue-specific manner.

Introns. Generally, optimal expression in monocotyledonous plants is obtained when an intron sequence is inserted between the promoter sequence and the structural gene sequence. An example of such an intron sequence is the HSP 70 intron described in WO 93/19189.

Polyadenylation signal. The DNA constructs of the present invention can possess a 3' untranslated region which functions in plants to direct the addition of polyadenylate nucleotides to the 3' end of the RNA. An example of a suitable 3' untranslated region is the polyadenylation signal of the Agrobacterium tumor inducing plasmid, ie., nopaline synthatase (NOS) gene.

Plastid targeting sequence. The DNA constructs of the present invention can optionally contain a plastid targeting sequence. The plastid targeting sequence directs the import of the protein into the plastid, and is removed during importation. The plastid targeting sequence can be, but is not limited to, the native chloroplast targeting peptide (CTP) identified in the C. sorokiniana NADP-GDH full-length cDNAs which encode the precursor proteins. A fusion of a selected plastid targeting sequence and the mature α- and β-NADP-GDH subunit sequences can be made by standard procedures and used in the present invention. GDH subunits lacking these targeting sequences are typically found in the cytoplasm of the cell. Such a cytosolic localized enzyme can be useful in capturing ammonium or glutamate compartmentalized in the cytosol of the cell.

GDH gene sources. The GDH gene used in the DNA constructs of the present invention can be any GDH gene. It is not limited to the *C. sorokiniana* GDH genes described above, although they are preferred. For example, a GDH gene from bacteria or fungi can be used. The examples provided use the α- and β-GDH genes of *C. sorokiniana*, but should not be interpreted in any way to limit the scope of the present invention. Individuals skilled in the art will recognize that various other genes as well as alterations can be made to genes and methods described herein while not departing from the spirit and scope of the present invention. For example, mutagenesis and routine screening can be implemented by techniques well known in the art to produce mutant variants that lack regulation by the cofactor NADPH.

Transient expression in maize protoplasts. In order to test the expression of the *C. sorokiniana* GDH subunits and their assembly into active enzymes in *Zea mays* cells, vectors were constructed to contain the CaMV E35S promoter, the coding sequence for the mature α-subunit (pMON21904) or β- subunit (pMON21905), the NOS 3'-untranslated polyadenylation region, and kanamycin resistance for selection in *E. coli*. The α- and β-subunit genes were isolated as a XbaI-EcoRI fragment from pET 11a-α-cDNA and pET 11a-β-cDNA, respectively. The GDH genes were ligated into the XbaI-EcoRI E35S promoter, NOS 3', kanamycin resistance bearing region of pMON22072 to give pMON21904, and pMON21905. The DNA constructs were electroporated into maize and wheat protoplast according to the method of Sheen et al. (*The Plant Cell* Vol. 3, 225–245).

Analysis of transformed maize protoplasts. Pelleted protoplast samples transformed with pMON21904 (α-subunit), pMON21905 (β-subunit), pMON21709 (kanamycin negative control DNA), and no DNA were thawed in 0.2 mL of GDH cell breakage buffer (Yeung et al., supra) on ice. The cells in each suspension were homogenized twice for 30 seconds, chilled on ice, and clarified at 14,000 rpm for 10 minutes. Cell extracts were assayed in the deaminating direction at 38.5° C. according to Yeung et al., supra. Total protein content of the cell extracts was determined using the BioRad microprotein assay according to the manufacturer's protocol. Activities were normalized against total protein content for comparisons among different preparations. One unit of GDH activity is defined as the amount of enzyme necessary to reduce 1 μmol of NADP per minute at 38.5° C.

Protoplasts transformed with the control vector pMON21709 (n=3) or protoplasts not transformed (n=3) had no detectable NADP-GDH activity. Protoplasts transformed with pMON21904 (n=3) expressed 3.31 Units $mg^{-1}$ protein of GDH activity, whereas pMON21905 transformed protoplasts (n=3) 1.96 Units $mg^{-1}$ protein.

The high level of activity observed for the protoplasts transformed with the cytoplasmic expressed *C. sorokiniana* α- and β-NADP-GDH genes provides evidence that the GDH subunits are expressed in heterologous plant systems. Additionally, expression levels demonstrate that the subunits are assembled into active enzymes. Generally, it would be readily apparent to persons of ordinary skill in the art that superfluous sequences added to the described sequences, or fragments of the nucleotide or amino acid sequences described herein, which result in polynucleotides or amino acid sequences that function similarly or equivalently to the sequences expressly described herein, should also be considered part of this invention. They can easily and routinely be produced by techniques well known in the art, for example, by time-controlled Bal31 exonuclease digestion of the full-length DNA, followed by expression of the resulting fragments and routine screening of the expression products as described in the foregoing example. In addition, it would be readily accepted by ordinarily skilled artisans that the function, property, or utility of the described sequences can be negatived by inserting mutations into the sequences by standard techniques and procedures. These mutations which, by implication, effectively serve to remove the property or function inherent in the sequences as described are hereby expressly included as part of the invention. For example, a clear distinction between the α- and β-subunits of the *C. sorokiniana* is the 11-amino acid polypeptide sequence at the N-terminus of the α-subunit, but absent in the β-subunit. This sequence can affect the affinity, specificity, and modulation of ammonium compounds by the enzyme. Therefore, it would be apparent that inserting (if absent) or removing (if present) the appropriate sequence, or its functional equivalent, to effect a difference in certain characteristics of other GDH genes, or their products, would be easily carried out by those persons.

It should also be understood that the examples and embodiments described herein are for illustrative purposes only and that various modifications or changes in light thereof will be suggested to persons skilled in the art and are to be included within the spirit and purview of this application and the scope of the appended claims.

We claim:

1. An isolated polynucleotide comprising a nucleotide sequence encoding an amino acid sequence selected from the group consisting of SEQ ID NO: 2, SEQ ID NO: 4, SEQ ID NO: 24, SEQ ID NO: 26, and fragments of any of the foregoing sufficient to exhibit α-GDH activity, β-GDH activity, or chloroplast-transit peptide activity, whereby the expression product of said polynucleotide exhibits α-GDH activity, β-GDH activity, or chloroplast transit peptide activity.

2. An isolated polynucleotide comprising a nucleotide sequence selected from the group consisting of SEQ ID NO: 1, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, and SEQ ID NO: 25.

3. The polynucleotide, according to claim 2, comprising a nucleotide sequence selected from the group consisting of the nucleotide sequences shown in SEQ ID NO: 1, SEQ ID NO: 3, SEQ ID NO: 23, and SEQ ID NO: 25.

4. The polynucleotide according to claim 1, comprising a chimeric construct capable of expressing in plant cells, said construct comprising a plant expressible promoter operably linked to said nucleotide sequence.

5. The polynucleotide, according to claim 4, wherein said nucleotide sequence is operably linked to a plant polyadenylation sequence.

6. A method for increasing assimilation of nitrogen in plant cells, said method comprising transforming a plant cell to comprise a polynucleotide encoding a polypeptide having glutamate dehydrogenase activity, and culturing said cell under conditions whereby descendent cells comprising said polynucleotide are produced and wherein said polynucleotide is expressed.

7. The method, according to claim 6, wherein said polynucleotide is operably linked to a plant expressible promoter.

8. The method, according to claim 6, wherein said polynucleotide is operably linked to a plant polyadenylation sequence.

9. A method for increasing assimilation of nitrogen in a plant, said method comprising expressing in said plant a polynucleotide encoding the amino acid sequence selected from the group consisting of SEQ ID NO: 2, SEQ ID NO: 4, SEQ ID NO: 24, and SEQ ID NO: 26, and fragments of any of the foregoing sufficient to exhibit α-GDH activity, β-GDH activity, or chloroplast transit peptide activity.

10. A transformed host cell comprising the polynucleotide of claim 1.

11. The transformed host cell, according to claim 10, wherein said polynucleotide comprises a nucleotide sequence selected from the group consisting of the nucleotide sequences shown in SEQ ID NO. 1, SEQ ID NO. 3, SEQ ID NO. 23, and SEQ ID NO. 25.

12. An isolated polynucleotide sequence encoding a chloroplast-transit peptide, said nucleotide sequence comprising a 5'-terminus sequence selected from SEQ ID NO. 1 and SEQ ID NO. 3.

13. A transformed host cell comprising the polynucleotide of claim 2.

* * * * *